United States Patent
Kun et al.

(10) Patent No.: US 7,405,227 B2
(45) Date of Patent: Jul. 29, 2008

(54) TREATMENT OF CANCER

(75) Inventors: Ernest Kun, Mill Valley, CA (US); Jerome Mendeleyev, San Francisco, CA (US); Carol Basbaurn, San Francisco, CA (US); Hassan Lemjabbar-Alaoui, Foster City, CA (US); Valeria Ossovskaya, San Francisco, CA (US)

(73) Assignee: BiPAr Sciences, Inc., Brisbane, CA (US)

( * ) Notice: Subject to any disclaimer, the term of this patent is extended or adjusted under 35 U.S.C. 154(b) by 0 days.

(21) Appl. No.: 11/458,379

(22) Filed: Jul. 18, 2006

(65) Prior Publication Data
US 2007/0015837 A1 Jan. 18, 2007

Related U.S. Application Data

(60) Provisional application No. 60/700,446, filed on Jul. 18, 2005.

(51) Int. Cl.
*A01N 43/42* (2006.01)
*A01N 43/16* (2006.01)
*C07D 217/22* (2006.01)
*C07D 311/02* (2006.01)

(52) U.S. Cl. ............... 514/309; 514/456; 546/141; 549/287

(58) Field of Classification Search ........... 514/309
See application file for complete search history.

(56) References Cited

U.S. PATENT DOCUMENTS

| | | | |
|---|---|---|---|
| 5,232,735 A | 8/1993 | Kurtz et al. | |
| 5,464,871 A * | 11/1995 | Kun et al. ............ | 514/617 |
| 5,482,975 A | 1/1996 | Kun et al. | |
| 5,484,951 A * | 1/1996 | Kun et al. ............ | 549/285 |
| 5,516,941 A | 5/1996 | Kun et al. | |
| 5,631,038 A | 5/1997 | Kurtz et al. | |
| 5,631,231 A | 5/1997 | Kurtz et al. | |
| 5,631,232 A | 5/1997 | Kurtz et al. | |
| 5,631,240 A | 5/1997 | Kurtz et al. | |
| 5,631,252 A | 5/1997 | Kurtz et al. | |
| 5,631,272 A | 5/1997 | Kurtz et al. | |
| 5,631,292 A | 5/1997 | Kurtz et al. | |
| 5,631,294 A | 5/1997 | Kurtz et al. | |
| 5,631,295 A | 5/1997 | Kurtz et al. | |
| 5,631,299 A | 5/1997 | Kurtz et al. | |
| 5,633,282 A | 5/1997 | Collins et al. | |
| 5,637,618 A | 6/1997 | Kurtz et al. | |
| 5,639,788 A | 6/1997 | Kurtz et al. | |
| 5,641,795 A | 6/1997 | Kurtz et al. | |
| 5,641,799 A | 6/1997 | Kurtz et al. | |
| 5,641,811 A | 6/1997 | Kurtz et al. | |
| 5,641,812 A | 6/1997 | Kurtz et al. | |
| 5,643,894 A | 7/1997 | Kurtz et al. | |
| 5,643,941 A | 7/1997 | Kurtz et al. | |
| 5,643,945 A | 7/1997 | Kurtz et al. | |
| 5,643,955 A | 7/1997 | Kurtz et al. | |
| 5,643,956 A | 7/1997 | Kurtz et al. | |
| 5,646,122 A | 7/1997 | Kurtz et al. | |
| 5,650,403 A | 7/1997 | Kurtz et al. | |
| 5,652,367 A * | 7/1997 | Kun et al. ............ | 546/141 |
| 5,654,311 A | 8/1997 | Kurtz et al. | |
| 5,665,755 A | 9/1997 | Kurtz et al. | |
| 5,670,518 A | 9/1997 | Kun et al. | |
| 5,700,792 A | 12/1997 | Kurtz et al. | |
| 5,703,053 A | 12/1997 | Kurtz et al. | |
| 5,753,674 A | 5/1998 | Kun et al. | |
| 5,837,729 A | 11/1998 | Bourinbaiar | |
| 5,866,608 A | 2/1999 | Kurtz et al. | |
| 5,874,444 A * | 2/1999 | West ................. | 514/310 |

(Continued)

FOREIGN PATENT DOCUMENTS

CN 1768733 5/2006

(Continued)

OTHER PUBLICATIONS j. Med. Chem 1994 37, 2175.*

(Continued)

*Primary Examiner*—Ardin H. Marschel
*Assistant Examiner*—Shirley V Gembeh
(74) *Attorney, Agent, or Firm*—Albert P. Halluin; Matthew V. Grumbling; Wilson Sonsini Goodrich & Rosati

(57) ABSTRACT

Methods of treating ovarian cancer, endometrium cancer, cervical cancer, pancreatic cancer, bladder cancer, eve cancer, central nervous system cancer, thyroid cancer and lung cancer are disclosed. Specifically disclosed are methods of treating ovarian adenocarcinoma that has migrated into the abdominal cavity, a transitional cell carcinoma of the bladder, an epithelioid carcinoma in a pancreatic duct, an adenocarcinoma in a pancreatic duct, an adenocarcinoma in the cervical epithelium. The methods comprise administering to a patient a therapeutically effective amount of a compound of formula (Ia)

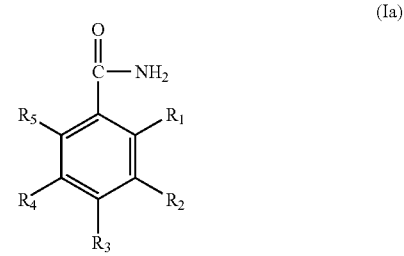

(Ia)

wherein $R_1$, $R_2$, $R_3$, $R_4$, and $R_5$ are described herein, wherein at least two of the five $R_1$, $R_2$, $R_3$, $R_4$, and $R_5$ substituents are always hydrogen, at least one of the five substituents is always nitro, and at least one substituent positioned adjacent to a nitro is always iodo, and pharmaceutically acceptable salts thereof.

8 Claims, 18 Drawing Sheets

U.S. PATENT DOCUMENTS

| | | | |
|---|---|---|---|
| 5,877,185 A * | 3/1999 | Kun et al. | 514/309 |
| 5,908,861 A | 6/1999 | Kun | |
| 6,004,978 A | 12/1999 | Kun et al. | |
| 6,008,250 A | 12/1999 | Kurtz et al. | |
| 6,015,792 A | 1/2000 | Kurtz et al. | |
| 6,303,629 B1 | 10/2001 | Kun | |
| 2005/0059824 A1 | 3/2005 | Vaidyanathan et al. | |
| 2005/0113283 A1 | 5/2005 | Solow-Cordero et al. | |
| 2007/0015837 A1 | 1/2007 | Kun et al. | |

FOREIGN PATENT DOCUMENTS

| | | |
|---|---|---|
| FR | 2456731 | 12/1980 |
| JP | 2000191612 | 7/2000 |
| JP | 2005336083 | 12/2005 |
| WO | 94/27584 | * 12/1994 |
| WO | WO 94/27584 | 12/1994 |
| WO | WO 97/34593 | 9/1997 |
| WO | WO 01/04086 | 1/2001 |
| WO | WO 02/49992 | 6/2002 |
| WO | WO 03/007955 | 1/2003 |

OTHER PUBLICATIONS

Wolff, Manfred E. Burger's Medicinal Chemistry, fifth edition, John Wiley & Sons, 1995, pp. 975-977.*

Banker, G.S. et al, "Modern Pharmaceutics, third edition.", Marcel Dekker, New York, 1996, p. 596.*

Erowld (2001) Introduction to the Federal Controlled Substance Analogue Act (pp. 1-4).*

Green facts.org, 1 pge, Feb. 1, 2002.*

Chen, et al. Potential for selective modulation of glutathione in cancer chemotherapy. Chem Biol Interact. 1998; 111-112:263-75.

Mendeleyev, et al. Potential chemotherapeutic activity of 4-iodo-3-nitrobenzamide. Metabolic reduction to the 3-nitroso derivative and induction of cell death in tumor cells in culture. Biochem Pharmacol. 1995; 50(5):705-14.

Rice, et al. Induction of Endonuclease-Mediated Apoptosis in Tumor Cells by C-Nitroso- Substituted Ligands of Poly(ADP-Ribose) Polymerase. Proceedings of the National Academy of Sciences. 1992; 89:7703-7707.

Astrazeneca International. Gefitinib (Iressa™) Lung Cancer ISEL Trial shows no overall survival advantage in a highly refractory population. Press release, Dec. 17, 2004. Available at: http://www.astrazeneca.com.pressrelease/4245.aspx Last accessed Mar. 4, 2008.

Bigler, et al. Evaluation of tamoxifen in persistent or recurrent nonsquamous cell carcinoma of the cervix: a Gynecologic Oncology Group study. International Journal of Gynecological Cancer 2004;14(5):871-874.

Chustecka, Z. Adding Bevacizumab Not Beneficial in Pancreatic Cancer. 2007 Gastrointestinal Cancers Symposium. Presented Jan. 20, 2007.

Crowson, et al. A phase II study to evaluate tamoxifen in pancreatic adenocarcinoma. Eur J Surg Oncol. 1986;12(4):335-6.

Dongiovanni, et al. Gefitinib (ZD1839): Therapy in selected patients with non-small cell lung cancer (NSCLC)? Lung Cancer. Feb. 1, 2008 [Epub ahead of print] Availabel at: http://www.ncbi.nlm.gov/pubmed/18243402 Last accessed Mar. 5, 2008.

Duell, et al. A population-based study of the Arg399Gln polymorphism in X-ray repair cross-complementing group 1 (XRCC1) and risk of pancreatic adenocarcinoma. Cancer Res 2002;62:4630-6.

Early Breast Cancer Trialists' Collaborative Group. Tamoxifen for early breast cancer. The Cochrane Database of Systematic Reviews 2008 Issue 1. Available at: http://www.cochrane.org/reviews/en/ab000486.html. Last accessed Mar. 4, 2008.

Edwards, et al. Resistance to therapy caused by intragenic deletion in BRCA2. Nature. 2008;451(7182):1111-5.

Fierce Biotech. Avastin encounters rare failure for pancreatic cancer. Fierce Biotech Web site. Jun. 26, 2006. Available at: http://www.fiercebiotech.com/story/avastin-encounters-rare-failure-for-pancreatic-cancer/2006-06-27 Last accessed Mar. 4, 2008.

Fisher, et al. Endometrial cancer in tamoxifen-treated breast cancer patients: findings from the National Surgical Adjuvant Breast and Bowel Project (NSABP) B-14. J Natl Cancer Inst 1994; 86:527-37.

Gurpide, E. Endometrial Cancer: Biochemical and Clinical Correlates. J Natl Cancer Inst 1991; 83(6): 405-416.

Hegi, et al. MGMT gene silencing and benefit from temozolomide in glioblastoma. N Engl J Med. 2005 10;352(10):997-1003.

Ishii, et al. Efficacy of temozolomine is correlated with 1p loss and methylation of the deoxyribonucleic acid repair gene MGMT in malignant gliomas. Neurol Med Chir (Tokyo). Aug. 2007;47(8):341-9.

Kume, et al. Mutations in the serine protease inhibitor Kazal type 1 (Spink1) gene in Japanese patients with pancreatitis. Pancreatology 2005;5:354-60.

Kurman, R.J. Blaustein's Pathology of the Female Genital Tract. 4th ed. Springer-Verlag. New-York 1994.

Li, et al. Pancreatic cancer. Lancet 2004;363:1049-57.

Marchesi, et al. Triazene compounds: mechanism of action and related DNA repair systems. Pharmacol. Res. Oct. 2007; 56(4):275-87.

National Cancer Institute. Bevacizumab Combined With Chemotherapy Improves Progression-Free Survival for Patients With Advanced Breast Cancer. U.S. National Institutes of Health. 2005. Available at: http://www.cancer.gov/newscenter/pressreleases/AvastinBreast. Last Accessed Mar. 4, 2008.

Paez, et al. EGFR mutations in lung cancer: correlation with clinical response to gefitinib therapy. Science. 2004 4;304(5676):1497-500.

Pao, et al. EGF receptor gene mutations are common in lung cancers from "never smokers" and are associated with sensitivity of tumors to gefitinib and erlotinib. Proc Natl Acad Sci U S A. Sep. 7, 2004;101(36):13306-11.

Porta, et al. Serum concentrations of organochlorine compounds and K-ras mutations in exocrine pancreatic cancer. PANKRAS II Study Group. Lancet 1999;354:2125-9.

Roche—Media News. US Phase III study of Avastin in advanced pancreatic cancer does not meet primary endpoint. Basel, Jun. 27, 2006. Roche Web site. Available at: http://www.roche.com/home/media/med-cor-2006/med-cor-2006-06-27.htm?printout=1 Last accessed Mar. 4, 2008.

Sakai, et al. Secondary mutations as a mechanism of cisplatin resistance in BRCA2-mutated cancers. Nature. Feb. 10, 2008;451:1116-21.

Shah, et al. Selenium disrupts estrogen receptor (alpha) signaling and potentiates tamoxifen antagonism in endometrial cancer cells and tamoxifen-resistant breast cancer cells. Mol Cancer Ther. 2005;4(8):1239-49.

Shaw, et al. Practice parameters in adults with suspected or known supratentorial nonoptic pathway low-grade glioma. Neurosurg. Focus. 4960, Article 10, 1998.

Tuma, et al. Targeting DNA Repair in BRCA Mutation Carriers. Oncoloy Times. Sep. 25, 2007;29(18):52-53.

Wiewrodt, et al. MGMT in primary and recurrent human glioblastomas after radiation and chemotherapy and comparison with p53 status and clinical outcome. Int J Cancer. Mar. 15, 2008;122(6):1391-9.

Williams, et al. Tamoxifen for relapse of ovarian cancer. Cochrane Database of Systematic Review 1998. Issue 2. Available at: http://www.cochrane.org/reviews/en/ab001034.html Last accessed Mar. 4, 2008.

* cited by examiner

BT474 - Breast cancer cell line

BP: 6-amino-5-iodo-benzopyrone
BA: 4-iodo-3-nitrobenzamide

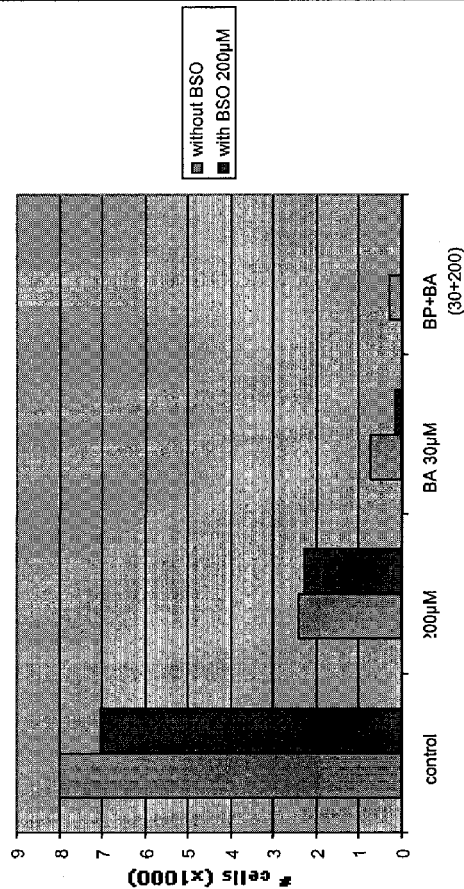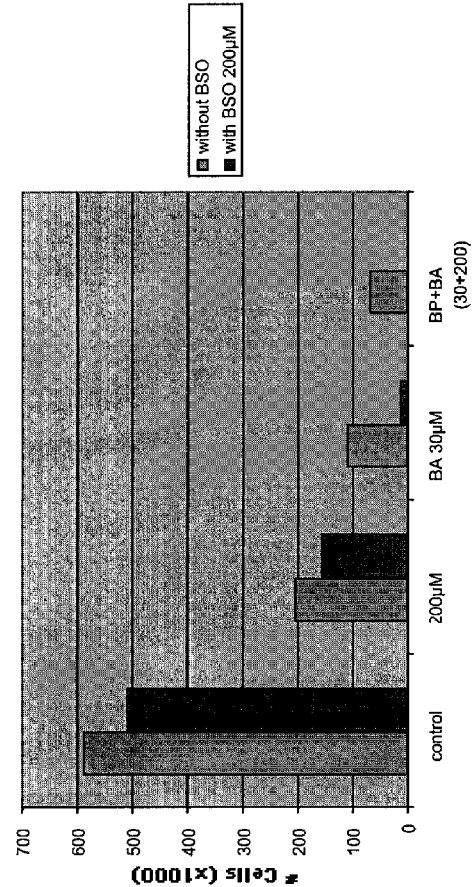
FIG. 2
Ovarian cancer cell lines
BP: 6-amino-5-iodo-benzopyrone
BA: 4-iodo-3-nitrobenzamide
BSO: Buthionine sulfoximine

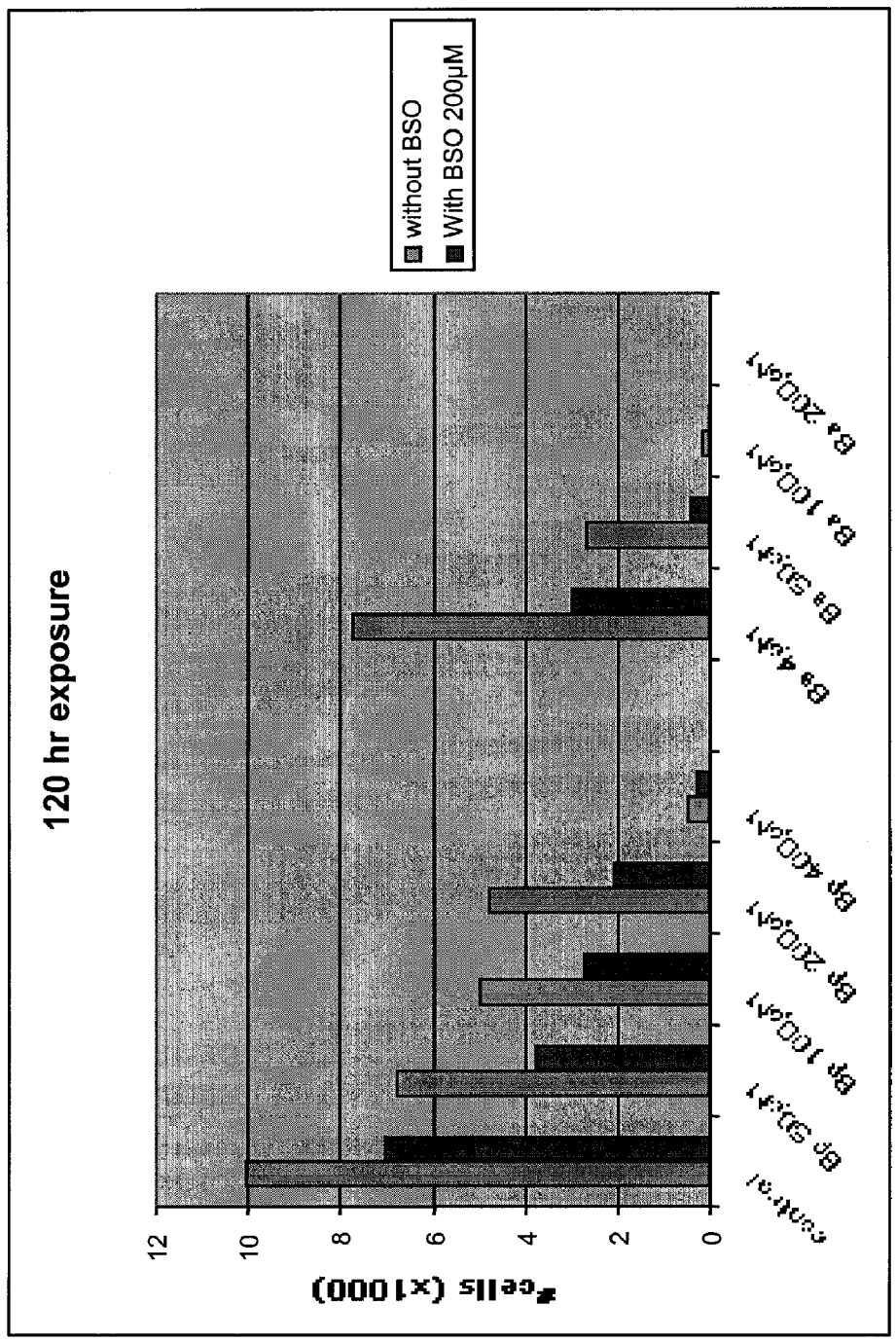

Lung cancer - NIH-292 cell line

Lung cancer NCA549 cells

Bladder Cancer (TCCSUP)

Bp: 6-amino-5-iodo-benzopyrone
Ba: 4-iodo-3-nitrobenzamide

Prostate cancer DUPRO Cells

Pancreatic cancer PANC1 cells

Pancreatic cancer CFPAC1 cells

Pancreatic cancer NOR-P1 cells

In vitro: Cervical cancer cells (Hela)

72 hours after treatment

BP: 6-amino-5-iodo-benzopyrone
BA: 4-iodo-3-nitrobenzamide
BSO: Buthionine sulfoximine 4-Iodo-3-nitrobenzamide demonstrates anti-tumor efficacy in OVCAR3 (human ovarian adenocarcinoma) xenograft model in nude mice BA: 4-iodo-3-nitrobenzamide

Body Weight

Body Weight

BA + BP in Vivo

In vivo: BP reduces tumor volume
(mammary xenograft)

BP: 6-amino-5-iodo-benzopyrone

TREATMENT OF CANCER

CROSS-REFERENCE

This application is related to and claims priority to U.S. Provisional Application No. 60/700,446, filed Jul. 18, 2005, which is incorporated herein by reference in its entirety.

BACKGROUND OF THE INVENTION

Cancer is a serious threat to modem society. Malignant cancerous growths, due to their unique characteristics, pose serious challenges for modern medicine. Their characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

There are many types of cancer, including, breast, lung, ovarian, bladder, prostate, pancreatic, cervical, and leukemia. Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas and can carry significant risks to the patient. Breast cancer surgery invariably involves removal of part of or the entire breast. Some surgical procedures for prostate cancer carry the risk of urinary incontinence and impotence. The procedures for lung cancer patients often have significant post-operative pain as the ribs must be cut through to access and remove the cancerous lung tissue. In addition, patients who have both lung cancer and another lung disease, such as emphysema or chronic bronchitis, typically experience an increase in their shortness of breath following the surgery.

Radiation therapy has the advantage of killing cancer cells but it also damages non-cancerous tissue at the same time. Chemotherapy involves the administration of various anti-cancer drugs to a patient but often is accompanied by adverse side effects.

Worldwide, more than 10 million people are diagnosed with cancer every year and it is estimated that this number will grow to 15 million new cases every year by 2020. Cancer causes six million deaths every year or 12% of the deaths worldwide. There remains a need for methods that can treat cancer. These methods can provide the basis for pharmaceutical compositions useful in the prevention and treatment of cancer in humans and other mammals.

A series of anti-tumor drugs have been identified. These drugs include nitro and nitroso compounds and their metabolites, which are the subject of U.S. Pat. No. 5,464,871 issued on Nov. 7, 1995 entitled "Aromatic Nitro and Nitroso Compounds and their Metabolites Useful as Anti-viral and Anti-tumor Agents," U.S. Pat. No. 5,670,518 issued on Sep. 23, 1997 entitled "Aromatic Nitro and Nitroso Compounds and their Metabolites Useful as Anti-viral and Anti-tumor Agents," U.S. Pat. No. 6,004,978 issued on Dec. 21, 1999 entitled "Methods of Treating Cancer with Aromatic Nitro and Nitroso Compounds and their Metabolites" the disclosures of which are incorporated herein by reference.

SUMMARY OF THE INVENTION

The present invention relates generally to methods of treatment of tumorigenic diseases using aromatic nitrobenzamide compounds and their metabolites. More specifically, it relates to the use of the nitro compound 4-iodo-3-nitrobenzamide or a salt, solvate, isomer, tautomer, metabolite, analog, or prodrug thereof in suppressing and inhibiting tumor growth in a mammal.

In one aspect of the invention, a method for treatment of cancer and disorders associated with cancer is provided comprising administering of pharmaceutical compositions comprising a compound of formula (Ia) with one or more additional pharmacologically active agents. In another aspect, a method for treatment of cancer and disorders associated with cancer is provided comprising administering a combination of a compound of formula (Ia) and buthionine sulfoximine (BSO). The compound of formula (Ia) can also be administered in combination with a benzopyrone compound of formula (II), with or without BSO.

In some preferred embodiments, the cancers are ovarian cancer, endometrium cancer, cervical cancer, pancreatic cancer, bladder cancer, eye cancer, central nervous system cancer, kidney cancer, thyroid cancer, and a lung cancer. In some preferred embodiments, the cancers are mammary gland ductal carcinoma, breast infiltrating carcinoma of lobular type, breast intraductal carcinoma, breast mucinous carcinoma, promyleocytic leukemia in the peripheral blood, an ovarian adenocarcinoma, an ovarian adenocarcinoma that has migrated into the abdominal cavity, a prostate adenocarinoma, a transitional cell carcinoma of the bladder, an epitheliod carcinoma in a pancreatic duct, an adenocarcinoma in a pancreatic duct, an adenocarcinoma in the cervical epithelium, and a lung cancer. In some preferred embodiments, the cancers are breast infiltrating carcinoma of lobular type, breast intraductal carcinoma and breast mucinous carcinoma. In some preferred embodiments, the cancers are colon cancer, prostate cancer, liver cancer, leukemia, glioma, and melanoma.

In some preferred embodiments of the abovementioned aspect of the present invention, the treatment further comprises surgery, radiation therapy, chemotherapy, gene therapy, immunotherapy, or a combination thereof. In some preferred embodiments, the administration of the compound is intravenous. In some preferred embodiments, a poly-ADP-ribose polymerase (PARP) molecule is inhibited by the compound of the present invention. In some preferred embodiments, a tumor cell undergoes apoptosis, cell cycle arrest, and/or necrosis in the subject after the administration of the compound of the present invention.

This invention relates to compositions of matter and pharmaceutical compositions, and to methods for their use in the treatment of cancer. For example, a composition of the invention can be a combination of two or more compounds described herein and/or a combination of two or more forms of a compound described herein. A pharmaceutical composition of the invention may be a composition suitable for administration to a subject.

BRIEF DESCRIPTION OF THE FIGURES

FIG. 2 depicts the effect of nitrobenzamide and benzopyrone compounds on the Ovcar3 and Skov3 ovarian cancer cell lines, with and without the co-treatment of BSO.

FIGS. 3A and 3B depicts the effect of nitrobenzamide and benzopyrone compounds on a lung cancer cell line, with and without the co-treatment of BSO.

DETAILED DESCRIPTION OF THE INVENTION

Definitions

Figure 1:
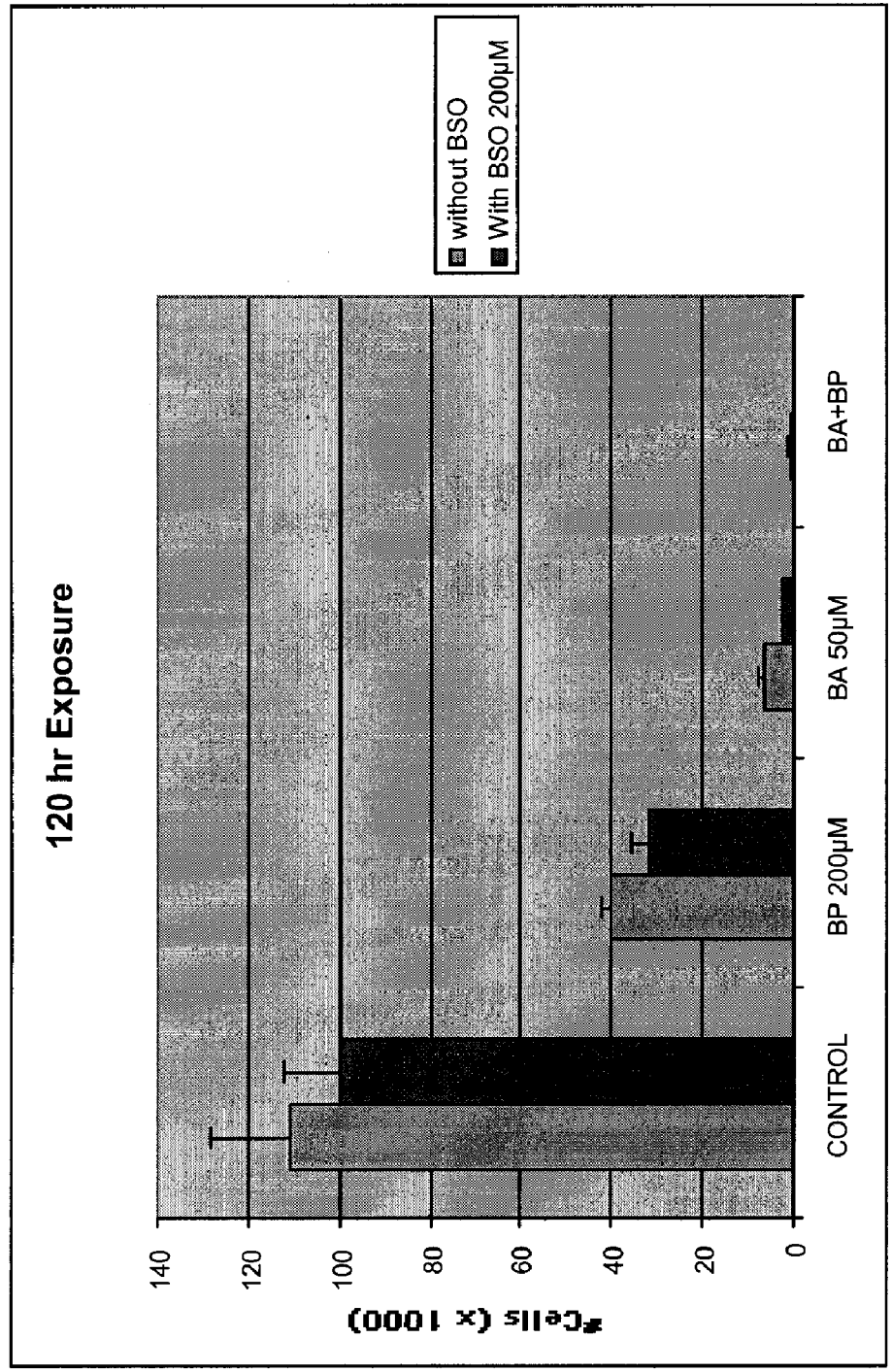
FIG. 1 depicts the effect of a nitrobenzamide compound on the BT474 breast cancer cell line, with and without the co-treatment of buthionine sulfoximine (BSO).
Figure 3B:
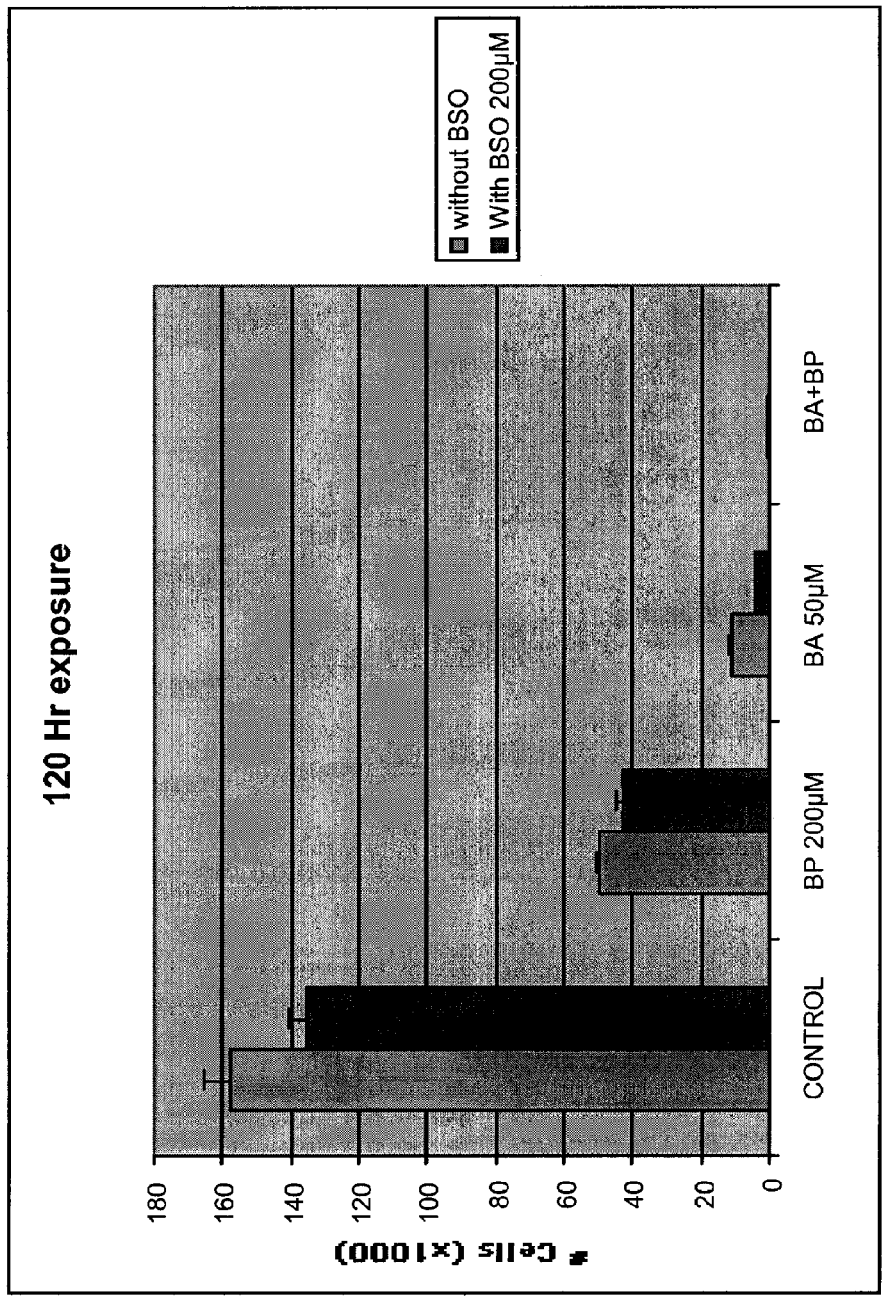
Figure 4:
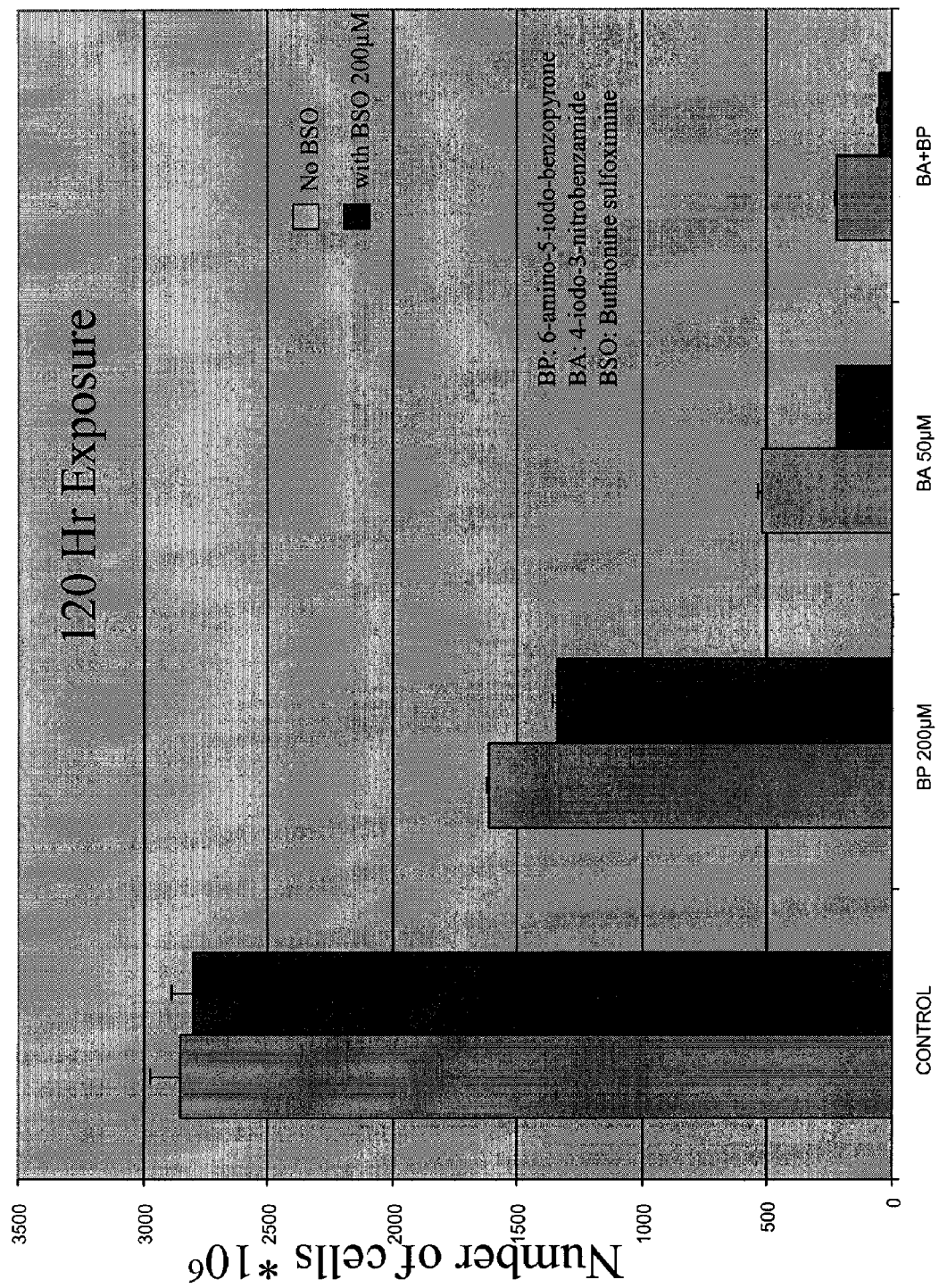
FIG. 4 depicts the effect of nitrobenzamide and benzopyrone compounds on a lung cancer cell line, with and without the co-treatment of BSO.
Figure 5:
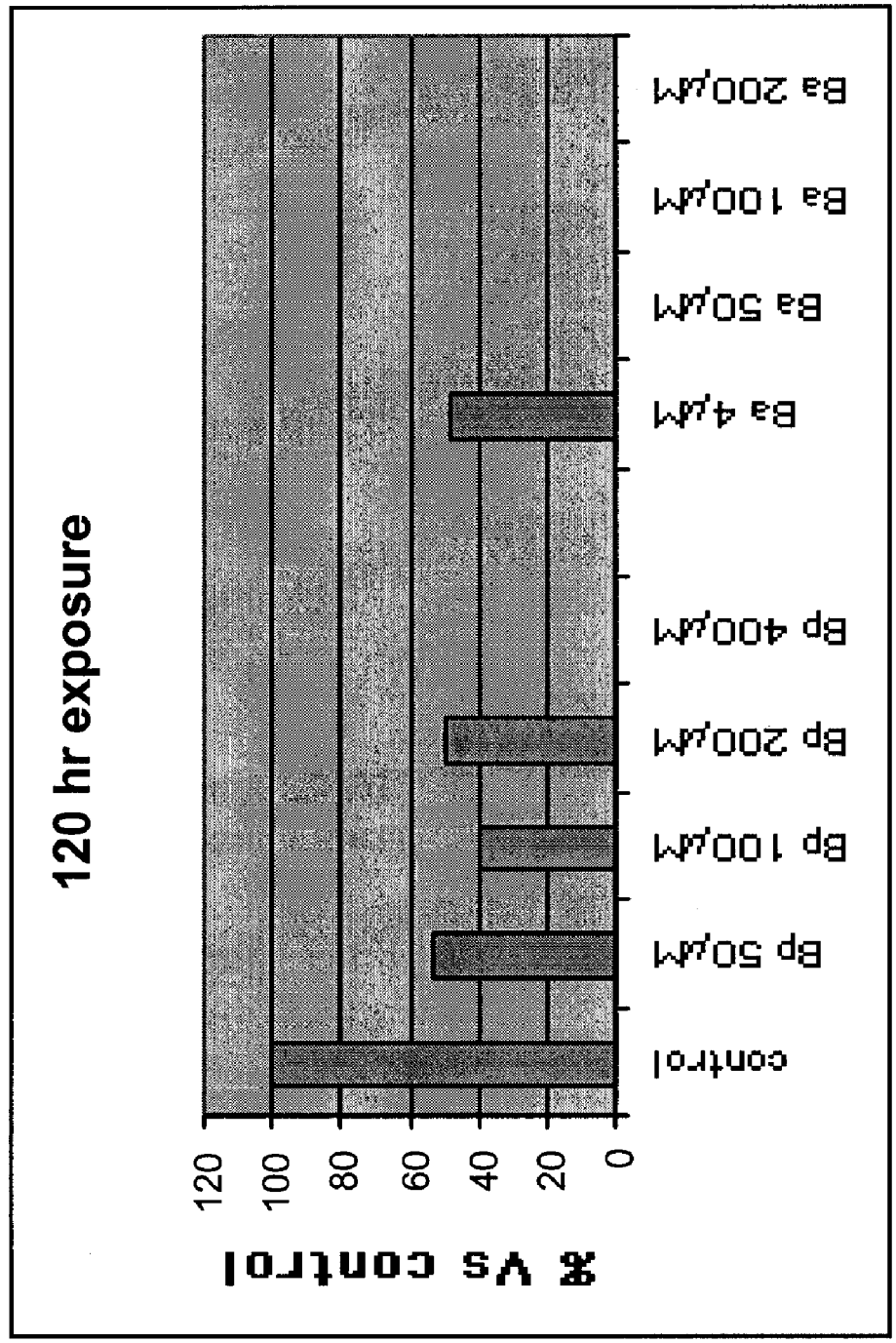
FIG. 5 depicts the effect of a nitrobenzamide compound on the TUCCSUP bladder cancer cell line.
Figure 6:
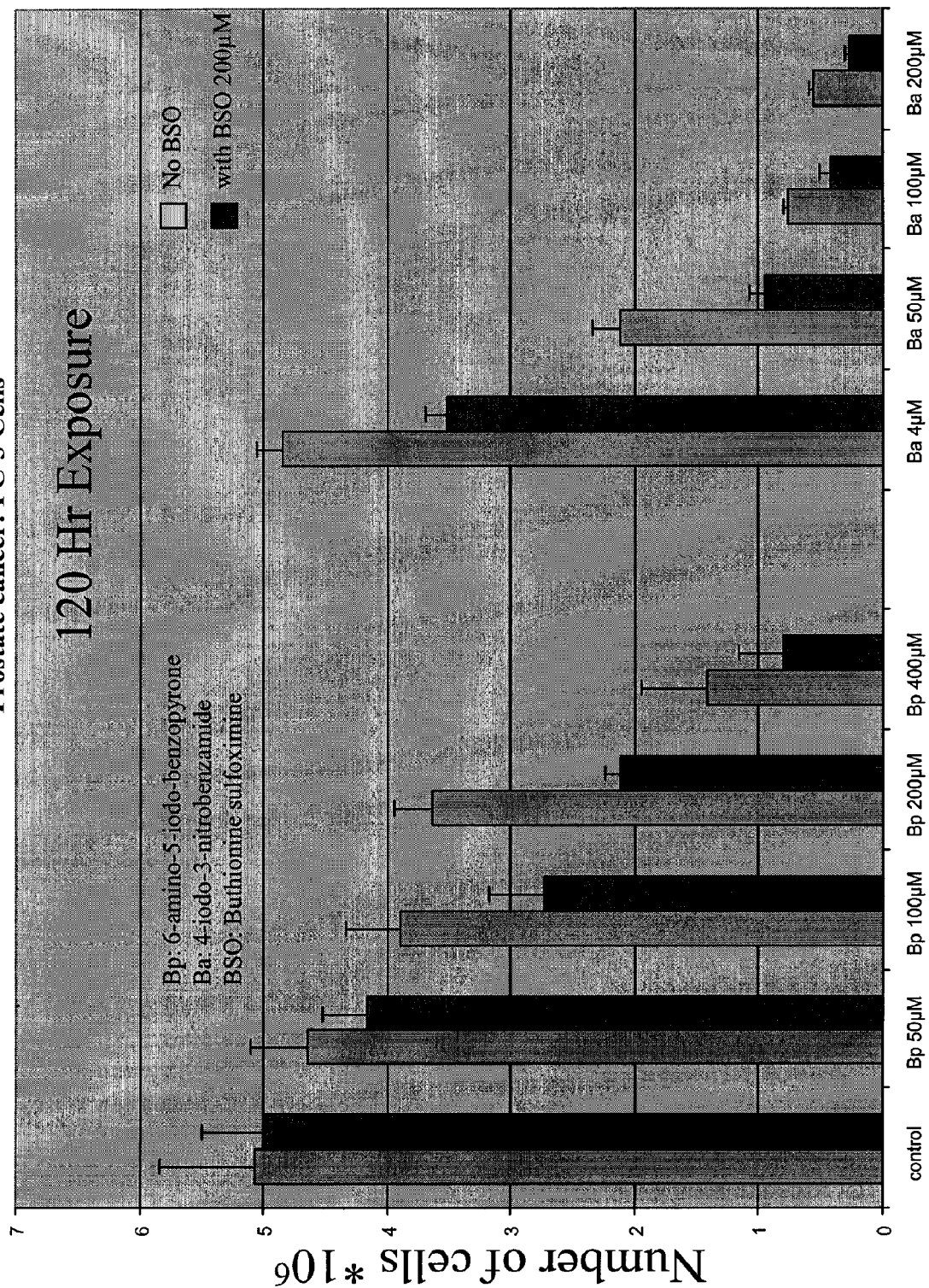
FIG. 6 depicts the effect of nitrobenzamide and benzopyrone compounds on a prostate cancer cell line, with and without the co-treatment of BSO.
Figure 7:
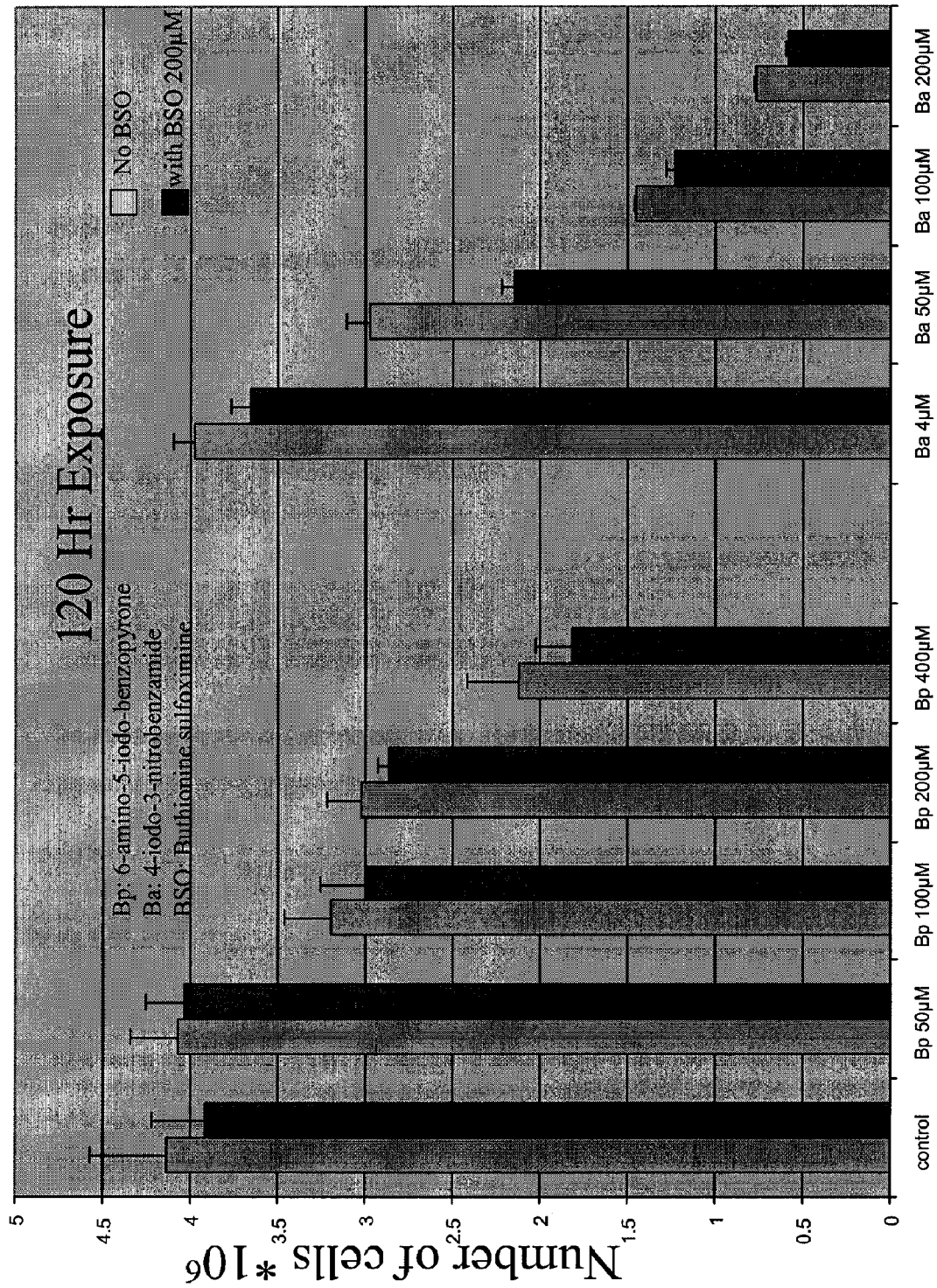
FIG. 7 depicts the effect of nitrobenzamide and benzopyrone compounds on a prostate cancer cell line, with and without the co-treatment of BSO.
Figure 8:
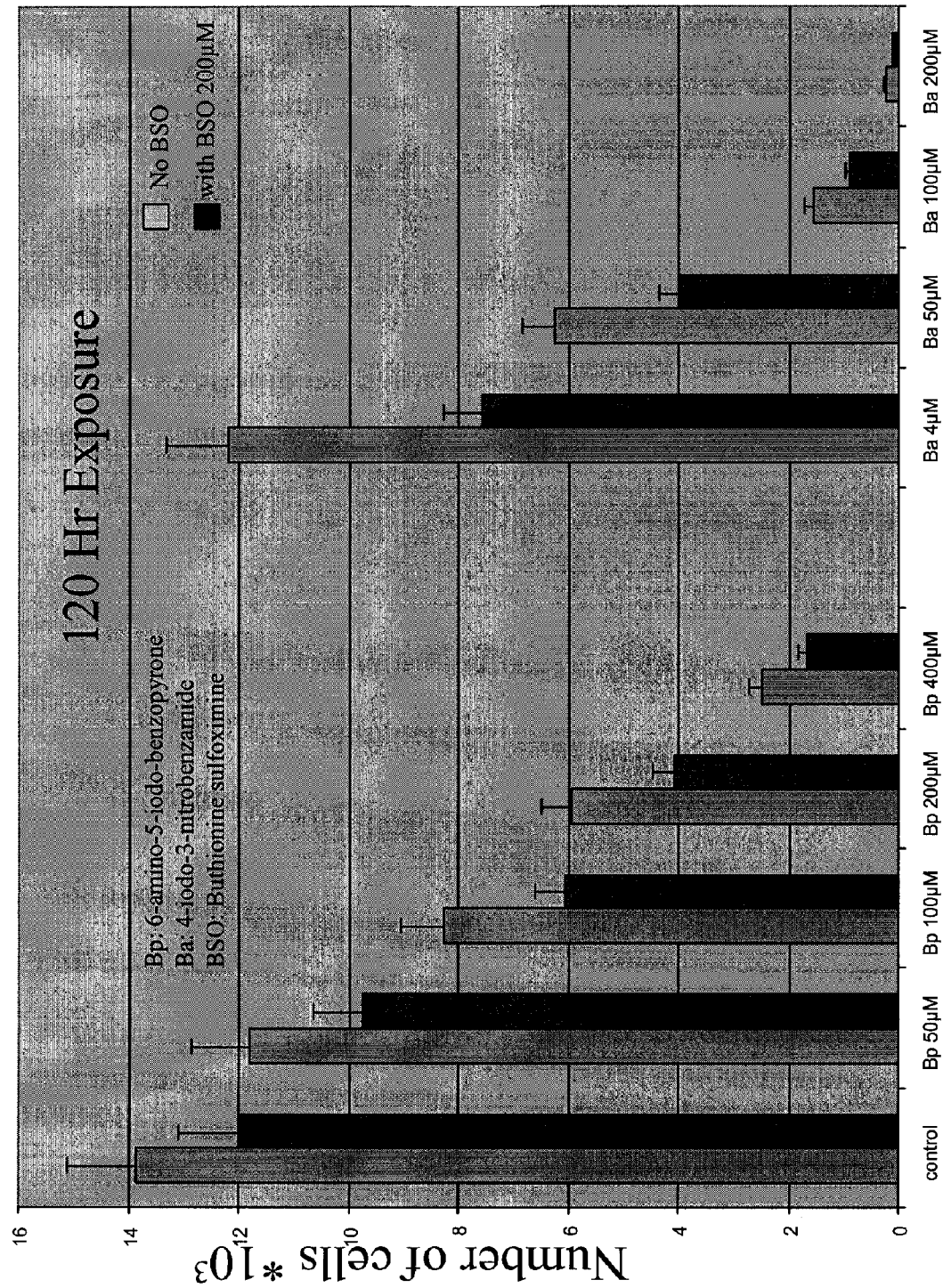
FIG. 8 depicts the effect of nitrobenzamide and benzopyrone compounds on a pancreatic cancer cell line, with and without the co-treatment of BSO.
Figure 9:
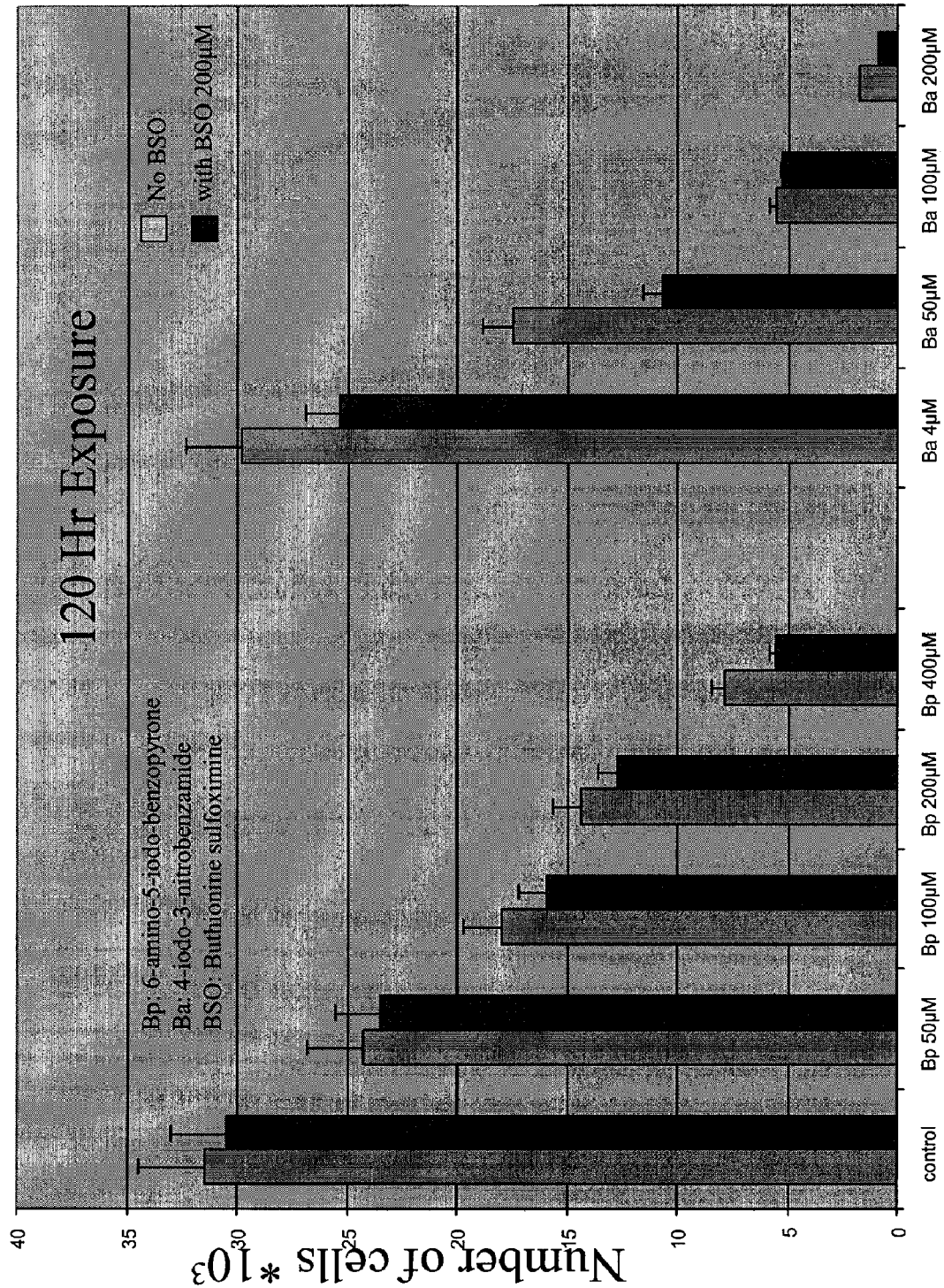
FIG. 9 depicts the effect of nitrobenzamide and benzopyrone compounds on a pancreatic cancer cell line, with and without the co-treatment of BSO.
Figure 10:
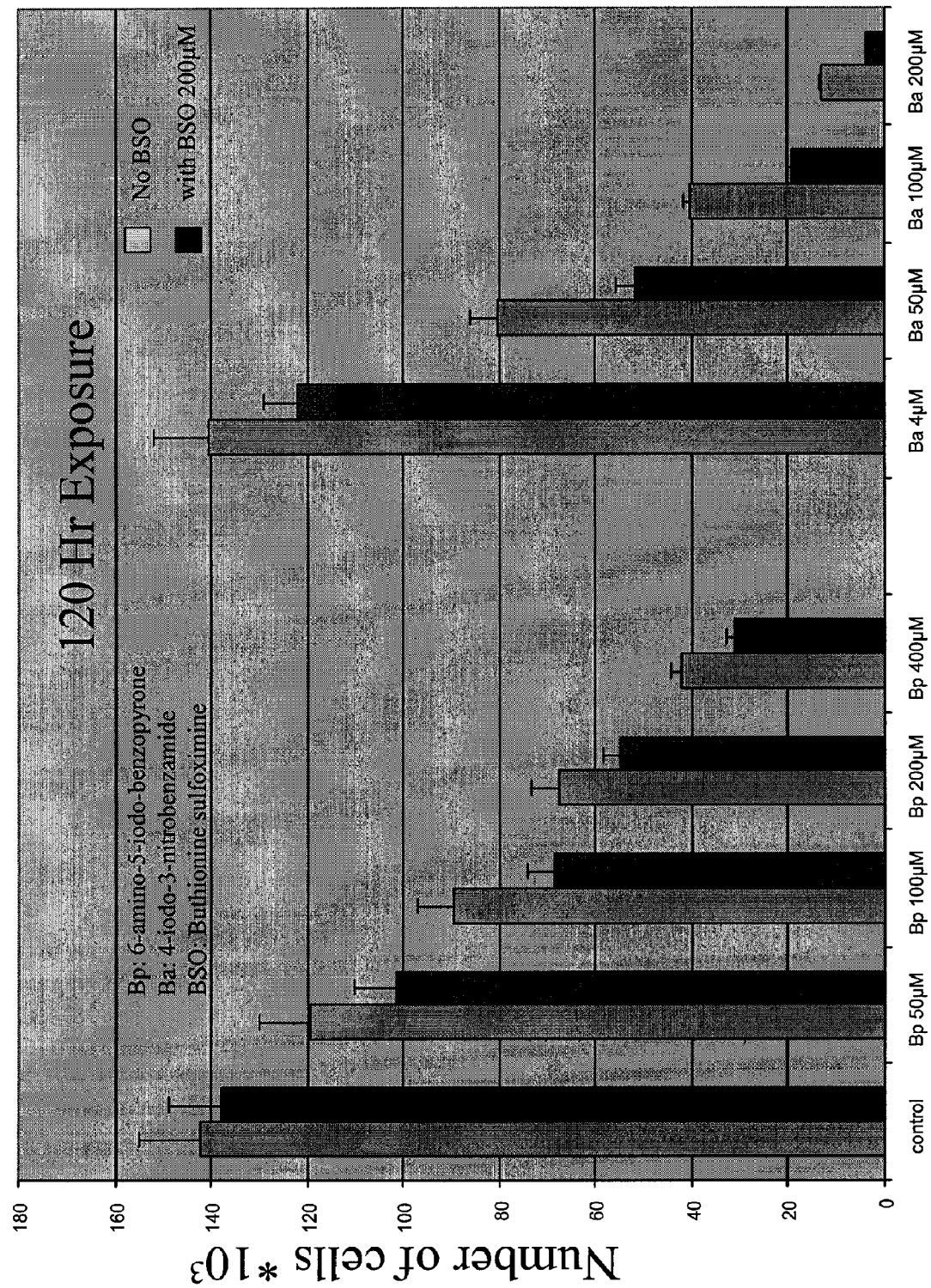
FIG. 10 depicts the effect of nitrobenzamide and benzopyrone compounds on a pancreatic cancer cell line, with and without the co-treatment of BSO.

"Nitrobenzamide compound(s)" means a compound of the formula (Ia)

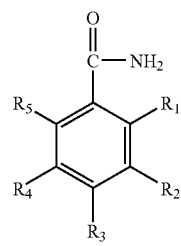

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of one or more anti-cancer drugs such as, antineoplastic chemotherapeutic agents, chemopreventative agents, and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The terms "effective amount" or "pharmaceutically effective amount" refer to a nontoxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a nitrobenzamide compound as disclosed herein per se or a composition comprising the nitrobenzamide compound herein required to provide a clinically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method of the invention may be performed on, or a composition of the invention administered to a patient at risk of developing cancer, or to a patient reporting one or more of the physiological symptoms of such conditions, even though a diagnosis of the condition may not have been made.

Nitrobenzamide Compounds

Compounds useful in the present invention are of Formula (Ia)

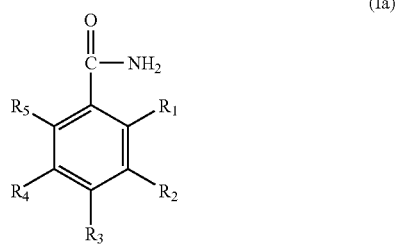

(Ia)

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo.

A preferred compound of formula Ia is

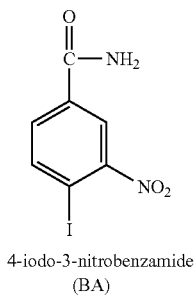

4-iodo-3-nitrobenzamide
(BA)

The present invention provides for the use of the aforesaid nitrobenzamide compounds for the treatment of breast cancers including a ductal carcinoma in a mammary gland, other forms of leukemia including acute promyleocytic leukemia in peripheral blood, ovarian cancer, lung cancer, bladder cancer, prostate cancer, pancreatic cancer, and cervical cancer, as well as other cancer types described herein (U.S. Pat. Nos. 5,464,871, 5,670,518, and 6,004,978 are incorporated herein by reference in their entirety). The present invention also provides the use of the aforesaid nitrobenzamide compounds for the treatment of Gleevac (Imanitib Mesylate) resistant patient population. Gleevec is a tyrosine kinase inhibitor.

In some preferred embodiments, the nitrobenzamide compounds of the present invention are used for the treatment of breast cancer, particularly, mammary gland ductal carcinoma, breast infiltrating carcinoma of lobular type, breast intraductal carcinoma and breast mucinous carcinoma. In some preferred embodiments, the nitrobenzamide compounds of the present invention are used for the treatment of ovarian and endometrial cancer. In still further preferred embodiments, the nitrobenzamide compounds of the present invention are used for the treatment of lung and colon cancer.

In some preferred embodiments, the nitrobenzamide compounds of the present invention are used for the treatment of bladder and prostate cancer. In some preferred embodiments, the nitrobenzamide compounds of the present invention are used for the treatment of liver and pancreatic cancer. In some preferred embodiments, the nitrobenzamide compounds of the present invention are used for the treatment of leukemia, cervical, glioma, and melanoma.

In still further preferred embodiments, the nitrobenzamide compounds of the present invention are used for the treatment of cancers derived from stem cells. In breast cancer and other malignancies, a proportion of tumour cells—'cancer stem cells'—have the capacity for extensive proliferation and transferral of the tumour. An alteration in stem cell fate and growth may play a role in tumorigenesis. Epithelial stem cells have a life-span at least as long as that of the organism, and thus they are thought to be susceptible to multiple genetic hits which cumulatively may result in tumor formation. Many cancers, such as those of the skin and colon, arise in tissues that are constantly replenished with cells throughout life. But the crucial mutations that lead to the disease are likely to have occurred during the tissues' formative period, when cells are dividing exponentially.

The stem cell compartment, now identified virtually in every tissue, can be defined as a subset of rare cells, endowed with the exclusive prerogative of self-renewal and persistence throughout the organism's life, in contrast with differentiated cells, which form the tissue bulk, but usually feature a post-mitotic behavior and a short lifespan. The fact that several mutations are necessary for a cell to become cancerous may suggest that in many tissues the mutations may accumulate in stem cells. As cancer stem cells self-renew, it follows that they may be derived either from self-renewing normal stem cells, or from more differentiated cells that acquire peculiar properties of stem cells. Consistently, a tumor can be conceived as a tissue, including both "differentiated" cells, and a subset of "cancer stem cells", which maintain the tumor mass, and are likely responsible for formation of secondary tumors (metastasis). Hence, nitrobenzamides of the present invention can be used to target cancers derived from stem cells.

The present invention discloses a nonclinical pharmacology of 4-iodo-3-nitrobenzamide (BA) in human tumor and normal primary cells and also in mice, rats, and dogs. In vitro BA inhibited the proliferation of a variety of human tumor cells including breast, colon, prostate, cervix, lung, ovarian, melanoma, lymphoma, and leukemia. In vivo BA was evaluated in several animal models of carcinogenesis. Once-daily or twice-weekly administration of BA inhibits tumor growth in the human ovarian adenocarcinoma xenograft model in both nude and SCID mice, and positively affects the survival rate of animals exposed to the drug given daily or twice weekly.

The twice weekly dosing of BA for 3 weeks followed by a one week washout period is based on the results of the preclinical evaluation of the efficacy and safety of BA.

It has been reported that nitrobenzamide compounds have selective cytotoxicity upon malignant cancer cells but not upon nonmalignant cancer cells. See Rice et at., *Proc. Natl. Acad. Sci. USA* 89:7703-7707 (1992). In one embodiment, the nitrobenzamide compounds utilized in the methods of the present invention may exhibit more selective toxicity towards tumor cells than non-tumor cells.

It has been reported that the anti-tumorigenicity of nitrobenzamide and nitrososbenzamide compounds is enhanced when BSO is co-administered to cancer cells. See Mendeleyev et al., *Biochemical Pharmacol.* 50(5):705-714 (1995). Buthionine sulfoximine (BSO) inhibits gamma-glutamylcysteine synthetase, a key enzyme in the biosynthesis of glutathione, which is responsible in part for cellular resistance to chemotherapy. See Chen et al., *Chem Biol Interact*. April 24;111-112:263-75 (1998). The invention also provides a method for treating cancer comprising the administration of a nitrobenzamide and/or benzopyrone compound in combination with BSO.

In addition to BSO, other inhibitors of gamma-glutamylcysteine synthetase can be used in combination with nitrobenzamide and/or benzopyrone compounds. Other suitable analogs of BSO include, but are not limited to, proprothionine sulfoximine, methionine sulfoximine, ethionine sulfoximine, methyl buthionine sulfoximine, γ-glutamyl-α-aminobutyrate and γ-glutamylcysteine.

Benzopyrone Compounds

In some embodiments, the benzamide compounds are administered in combination with benzopyrone compounds of formula II. The benzopyrone compounds of formula II are,

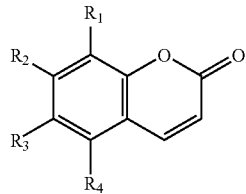

Formula II wherein $R_1$, $R_2$, $R_3$ and $R_4$ are independently selected from the group consisting of H, halogen, optionally substituted hydroxy, optionally substituted amine, optionally substituted lower alkyl, optionally substituted phenyl, optionally substituted $C_4$-$C_{10}$ heteroaryl and optionally substituted $C_3$-$C_8$ cycloalkyl or a salt, solvate, isomer, tautomers, metabolite, or prodrug thereof (U.S. Pat. No. 5,484,951 is incorporated herein by reference in its entirety).

In a preferred embodiment, the invention relates to the following benzopyrone compound of formula II

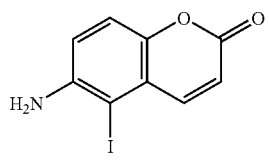

6-amino-5-iodo-benzopyrone
(BP)

Mechanism of Nitrobenzamide Compounds

Not intending to be limited by one mechanism of action, the compounds described herein are believed to have anticancer properties via the modulation of a poly (ADP-ribose) polymerase enzyme. The drugs' mechanism of action is related to their ability to act as a ligand for the nuclear enzyme poly (ADP-ribose) polymerase (PARP-1). See Mendeleyev et al., supra, (1995). PARP-1 is expressed in the nucleus and catalyzes the conversion of β-nicotinamide adenine dinucleotide ($NAD^+$) into nicotinamide and poly-ADP-ribose (PAR). PARP-1's role in homeostatic conditions seems to be limited to DNA transcription and repair. However, when cellular stress causes DNA damage, PARP-1 activity increases dramatically, which appears to be necessary for genomic integrity. Shall et at., *Mutat Res*. June 30;460(1):1-15 (2000).

One of PARP-1's functions is to synthesize the biopolymer, poly (ADP-ribose). Both poly (ADP-ribose) and PARP-1 have been linked to the repair of DNA repair, apoptosis, the maintenance of genomic stability, and carcinogenesis. See Masutani et al., *Genes, Chromosomes, and Cancer* 38:339-348 (2003). PARP-1 plays a role in DNA repair, specifically base excision repair (BER). BER is a protection mechanism in mammalian cells for single-base DNA breakage. PARP-1 binds to the ends of DNA fragments through its zinc finger domains with great affinity and thereby acts as a DNA damage sensor. Gradwohl et al., *Proc. Natl. Acad. Sci. USA* 87:2990-2994 (1990); Murcia et al., *Trends Biochem Sci* 19: 172-176 (1994). A breakage in the DNA triggers a binding response by PARP-1 to the site of the break. PARP-1 then increases its catalytic activity several hundred fold (See Simonin et al., *J Biol Chem* 278: 13454-13461 (1993)) and begins to convert poly ADP-ribosylation of itself (Desmarais et al., *Biochim Biophys Acta* 1078: 179-186 (1991)) and BER proteins, such as DNA-PKcs and the molecular scaffold protein XRCC-1. See Ruscetti et al., *J. Biol. Chem.* Jun 5;273 (23):14461-14467 (1998) and Masson et al., *Mol Cell Biol*. June;18(6):3563-71 (1998). BER proteins are rapidly recruited to the site of DNA damage. El-Kaminsy et al., *Nucleic Acid Res.* 31(19):5526-5533 (2003); Okano et al., *Mol Cell Biol.* 23(11):3974-3981 (2003). PARP-1's dissociates from the DNA breakage site but it remains in the vicinity of the DNA repair event.

Inhibiting the activity of a PARP molecule includes reducing the activity of these molecules. The term "inhibits" and its grammatical conjugations, such as "inhibitory," is not intended to require complete reduction in PARP activity. Such reduction is preferably by at least about 50%, at least about 75%, at least about 90%, and more preferably by at least about 95% of the activity of the molecule in the absence of the inhibitory effect, e.g., in the absence of an inhibitor, such as a nitrobenzamide compound of the invention. Most preferably, the term refers to an observable or measurable reduction in activity. In treatment scenarios, preferably the inhibition is sufficient to produce a therapeutic and/or prophylactic benefit in the condition being treated. The phrase "does not inhibit" and its grammatical conjugations does not require a complete lack of effect on the activity. For example, it refers to situations where there is less than about 20%, less than about 10%, and preferably less than about 5% of reduction in PARP activity in the presence of an inhibitor such as a nitrobenzamide compound of the invention.

Uses of the Benzamide Compounds

Cancer Types

The invention provides methods to treat several specific cancers or tumors. For example, cancer types include adrenal cortical cancer, anal cancer, aplastic anemia, bile duct cancer, bladder cancer, bone cancer, bone metastasis, Adult CNS brain tumors, Children CNS brain tumors, breast cancer, Castleman Disease, cervical cancer, Childhood Non-Hodgkin's lymphoma, colon and rectum cancer, endometrial cancer, esophagus cancer, Ewing's family of tumors, eye cancer, gallbladder cancer, gastrointestianl carcinoid tumors, gastrointestinal stromal tumors, gestational trophoblastic disease, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sacrcoma, vaginal cancer, vulvar cancer, and Waldenstrom's macroglobulinemia.

Carcinoma of the thyroid gland is the most common malignancy of the endocrine system. Carcinoma of the thyroid gland include differentiated tumors (papillary or follicular) and poorly differentiated tumors (medullary or anaplastic). Carcinomas of the vagina include squamous cell carcinoma, adenocarcinoma, melanoma and sarcoma. Testicular cancer is broadly divided into seminoma and nonseminoma types.

Thymomas are epithelial tumors of the thymus, which may or may not be extensively infiltrated by nonneoplastic lymphocytes. The term thymoma is customarily used to describe neoplasms that show no overt atypia of the epithelial component. A thymic epithelial tumor that exhibits clear-cut cytologic atypia and histologic features no longer specific to the thymus is known as a thymic carcinoma (also known as type C thymoma).

The methods provided by the invention may comprise the administration of the benzamide compounds in combination with other therapies. The choice of therapy that can be co-administered with the compositions of the invention will depend, in part, on the condition being treated. For example, for treating acute myeloid leukemia, a benzamide compound of some embodiments of the invention can be used in combination with radiation therapy, monoclonal antibody therapy, chemotherapy, bone marrow transplantation, gene therapy, immunotherapy, or a combination thereof.

Breast Cancer

In one aspect, the invention provides a method of treating breast cancer, preferably a ductal carcinoma in duct tissue in a mammary gland.

Several types of breast cancer exist that may be treated by the methods provided by the invention. A lobular carcinoma in situ and a ductal carcinoma in situ are breast cancers that have developed in the lobules and ducts, respectively, but have not spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that would benefit from treatment by the methods provided by the invention are medullary carcinomas, colloid carcinomas, tubular carcinomas, and inflammatory breast cancer.

Treatments available for breast cancer patients are surgery, immunotherapy, radiation therapy, chemotherapy, endocrine therapy, or a combination thereof. A lumpectomy and a mastectomy are two possible surgical procedures available for breast cancer patients.

Chemotherapy utilizes anti-tumor agents to prevent cancer cells from multiplying, invading, metastasizing and killing a patient. Several drugs are available to treat breast cancer, including cytotoxic drugs such as doxorubicin, cyclophosphamide, methotrexate, paclitaxel, thiotepa, mitoxantrone, vincristine, or combinations thereof. Endocrine therapy may be an effective treatment where the remaining breast tissue retains endocrine sensitivity. Agents administered for this therapy include tamoxifen, megestrol acetate, aminoglutethimide, fluoxymesterone, leuprolide, goserelin, and prednisone.

The methods provided by the invention can provide a beneficial effect for breast cancer patients, by administration of a nitrobenzamide compound or a combination of administration of a nitrobenzamide compound and surgery, radiation therapy, chemotherapy, or endocrine therapy.

Ovarian Cancer

In another aspect, the invention provides a method of treating ovarian cancer, including epithelial ovarian tumors. Preferably, the invention provides a method of treating an ovarian cancer selected from the following: an adenocarcinoma in the ovary and an adenocarcinoma that has migrated from the ovary into the abdominal cavity. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy.

Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy.

The methods provided by the invention can provide a beneficial effect for ovarian cancer patients, by administration of a nitrobenzamide compound or a combination of administration of a nitrobenzamide compound and surgery, radiation therapy, chemotherapy endocrine therapy, or a combination thereof.

Cervical Cancer

In another aspect, the invention provides a method of treating cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The chief treatments available for cervical cancer are surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that may be administered as part of chemotherapy to treat cervical cancer include cisplatin, carboplatin, hydroxyurea, irinotecan, bleomycin, vincrinstine, mitomycin, ifosfamide, fluorouracil, etoposide, methotrexate, and combinations thereof.

The methods provided by the invention can provide a beneficial effect for cervical cancer patients, by administration of a nitrobenzamide compound or a combination of administration of a nitrobenzamide compound and surgery, radiation therapy, chemotherapy, or a combination thereof.

Prostate Cancer

In one other aspect, the invention provides methods to treat prostate cancer, preferably a prostate cancer selected from the following: an adenocarcinoma or an adenocarinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

Surgery, immunotherapy, radiation therapy, cryosurgery, hormone therapy, and chemotherapy are some treatments available for prostate cancer patients. Possible surgical procedures to treat prostate cancer include radical retropubic prostatectomy, a radical perineal prostatectomy, and a laparscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells.

Hormone therapy, also called androgen deprivation therapy or androgen suppression therapy, may be used to treat prostate cancer. Several methods of this therapy are available including an orchiectomy in which the testicles, where 90% of androgens are produced, are removed. Another method is the administration of luteinizing hormone-releaseing hormone (LHRH) analogs to lower androgen levels. The LHRH analogs available include leuprolide, goserelin, triptorelin, and histrelin. An LHRH antagonist may also be administered, such as abarelix.

Treatment with an antiandrogen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB).

Chemotherapy may be appropriate where a prostate tumor has spread outside the prostate gland and hormone treatment is not effective. Anti-cancer drugs such as doxorubicin, estramustine, etoposide, mitoxantrone, vinblastine, paclitaxel, docetaxel, carboplatin, and prednisone may be administered to slow the growth of prostate cancer, reduce symptoms and improve the quality of life.

The methods provided by the invention can provide a beneficial effect for prostate cancer patients, by administration of a nitrobenzamide compound or a combination of administration of a nitrobenzamide compound and surgery, radiation therapy, chemotherapy, hormone therapy, or a combination thereof.

Pancreatic Cancer

In another aspect, the invention provides methods of treating pancreatic cancer, preferably a pancreatic cancer selected from the following: an epitheliod carcinoma in the pancreatic duct tissue and an adenocarcinoma in a pancreatic duct.

The most common type of pancreatic cancer is an adenocarcinoma, which occurs in the lining of the pancreatic duct. The possible treatments available for pancreatic cancer are surgery, immunotherapy, radiation therapy, and chemotherapy. Possible surgical treatment options include a distal or total pancreatectomy and a pancreaticoduodenectomy (Whipple procedure).

Radiation therapy may be an option for pancreatic cancer patients, specifically external beam radiation where radiation is focused on the tumor by a machine outside the body. Another option is intraoperative electron beam radiation administered during an operation.

Chemotherapy may be used to treat pancreatic cancer patients. Appropriate anti-cancer drugs include 5-fluorouracil (5-FU), mitomycin, ifosfamide, doxorubicin, steptozocin, chlorozotocin, and combinations thereof.

The methods provided by the invention can provide a beneficial effect for pancreatic cancer patients, by administration of a nitrobenzamide compound or a combination of administration of a nitrobenzamide compound and surgery, radiation therapy, or chemotherapy.

Bladder Cancer

In another aspect, the invention provides methods of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

To treat bladder cancer, surgery, radiation therapy, immunotherapy, chemotherapy, or a combination thereof may be applied. Some possible surgical options are a transurethral resection, a cystectomy, or a radical cystectomy. Radiation therapy for bladder cancer may include external beam radiation and brachytherapy.

Immunotherapy is another method that may be used to treat a bladder cancer patient. Typically this is accomplished intravesically, which is the administration of a treatment agent directly into the bladder by way of a catheter. One method is Bacillus Calmete-Guerin (BCG) where a bacterium sometimes used in tuberculosis vaccination is given directly to the bladder through a catheter. The body mounts an immune response to the bacterium, thereby attacking and killing the cancer cells.

Another method of immunotherapy is the administration of interferons, glycoproteins that modulate the immune response. Interferon alpha is often used to treat bladder cancer.

Anti-cancer drugs that may be used in chemotherapy to treat bladder cancer include thitepa, methotrexate, vinblastine, doxorubicin, cyclophosphamide, paclitaxel, carboplatin, cisplatin, ifosfamide, gemcitabine, or combinations thereof.

The methods provided by the invention can provide a beneficial effect for bladder cancer patients, by administration of a nitrobenzamide compound or a combination of administration of a nitrobenzamide compound and surgery, radiation therapy, immunotherapy, chemotherapy, or a combination thereof.

Acute Myeloid Leukemia

In another aspect, the invention provides methods of treating acute myeloid leukemia (AML), preferably acute promyleocytic leukemia in peripheral blood. AML begins in the bone marrow but can spread to other parts of the body including the lymph nodes, liver, spleen, central nervous system, and testes. It is acute meaning it develops quickly and may be fatal if not treated within a few months. AML is characterized by immature bone marrow cells usually granulocytes or monocytes, which continue to reproduce and accumulate.

AML may be treated by immunotherapy, radiation therapy, chemotherapy, bone marrow or peripheral blood stem cell transplantation, or a combination thereof. Radiation therapy includes external beam radiation and may have side effects. Anti-cancer drugs that may be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy may be used to treat AML patients. Small molecules or radioactive chemicals may be attached to these antibodies before administration to a patient in order to provide a means of killing leukemia cells in the body. The monoclonal antibody, gemtuzumab ozogamicin, which binds CD33 on AML cells, may be used to treat AML patients unable to tolerate prior chemotherapy regimens.

Bone marrow or peripheral blood stem cell transplantation may be used to treat AML patients. Some possible transplantation procedures are an allogenic or an autologous transplant.

The methods provided by the invention can provide a beneficial effect for leukemia patients, by administration of a nitrobenzamide compound or a combination of administration of a nitrobenzamide compound and surgery, radiation therapy, chemotherapy, or transplantation therapy.

There are other types of leukemia's that can also be treated by the methods provided by the invention including but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

Lung Cancer

In another aspect, the invention provides methods to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy.

Some anti-cancer drugs that may be used in chemotherapy to treat lung cancer include cisplatin, carboplatin, paclitaxel, docetaxel, gemcitabine, vinorelbine, irinotecan, etoposde, vinblastine, gefitinib, ifosfamide, methotrexate, or a combination thereof. Photodynamic therapy (PDT) may be used to treat lung cancer patients.

The methods provided by the invention can provide a beneficial effect for lung cancer patients, by administration of a nitrobenzamide compound or a combination of administration of a nitrobenzamide compound and surgery, radiation therapy, chemotherapy, photodynamic therapy, or a combination thereof.

Skin Cancer

In another aspect, the invention provides methods to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body. Different types of treatment are available for patients with non-melanoma and melanoma skin cancer and actinic keratosis including surgery, radiation therapy, chemotherapy and photodynamic therapy. Some possible surgical options for treatment of skin cancer are mohs micrographic surgery, simple excision, electrodesiccation and curettage, cryosurgery, laser surgery. Radiation therapy may be external beam radiation therapy or brachytherapy. Other types of treatments that are being tested in clinical trials are biologic therapy or immunotherapy, chemoimmunotherapy, topical chemotherapy with fluorouracil and photodynamic therapy.

The methods provided by the invention can provide a beneficial effect for skin cancer patients, by administration of a nitrobenzamide compound or a combination of administration of a nitrobenzamide compound and surgery, radiation therapy, chemotherapy, photodynamic therapy, or a combination thereof.

Eye Cancer, Retinoblastoma

In another aspect, the invention provides methods to treat eye retinoblastoma. Retinoblastoma is a malignant tumor of the retina. Although retinoblastoma may occur at any age, it most often occurs in younger children, usually before the age of 5 years. The tumor may be in one eye only or in both eyes. Retinoblastoma is usually confined to the eye and does not spread to nearby tissue or other parts of the body. Treatment options that attempt to cure the patient and preserve vision include enucleation (surgery to remove the eye), radiation therapy, cryotherapy, photocoagulation, immunotherapy, thermotherapy and chemotherapy. Radiation therapy may be external beam radiation therapy or brachytherapy.

The methods provided by the invention can provide a beneficial effect for eye retinoblastoma patients, by administration of a nitrobenzamide compound or a combination of administration of a nitrobenzamide compound and surgery, radiation therapy, cryotherapy, photocoagulation, thermotherapy and chemotherapy, or a combination thereof.

Eye Cancer, Intraocular Melanoma

In another aspect, the invention provides methods to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged. Treatments for intraocular melanoma include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy may be external beam radiation therapy or brachytherapy. Laser therapy may be an intensely powerful beam of light to destroy the tumor, thermotherapy or photocoagulation.

The methods provided by the invention can provide a beneficial effect for intraocular melanoma patients, by administration of a nitrobenzamide compound or a combination of administration of a nitrobenzamide compound and surgery, radiation therapy and laser therapy, or a combination thereof.

Endometrium Cancer

In another aspect, the invention provides methods to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

The methods provided by the invention can provide a beneficial effect for endometrium cancer patients, by administration of a nitrobenzamide compound or a combination of administration of a nitrobenzamide compound and surgery, radiation therapy, chemotherapy, gene therapy, photodynamic therapy, antiangiogenesis therapy, and immunotherapy, or a combination thereof.

Liver Cancer

In another aspect, the invention provides methods to treat primary liver cancer (cancer that begins in the liver). Primary liver cancer can occur in both adults and children. Different types of treatments are available for patients with primary liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for liver cancer patients, by administration of a nitrobenzamide compound or a combination of administration of a nitrobenzamide compound and surgery, radiation therapy, chemotherapy, percutaneous ethanol injection, hyperthemia therapy and immunotherapy, or a combination thereof.

Kidney Cancer

In another aspect, the invention provides methods to treat kidney cancer. Kidney cancer (also called renal cell cancer or renal adenocarcinoma) is a disease in which malignant cells are found in the lining of tubules in the kidney. Kidney cancer may be treated by surgery, radiation therapy, chemotherapy and immunotherapy. Some possible surgical options to treat kidney cancer are partial nephrectomy, simple nephrectomy and radical nephrectomy. Radiation therapy may be external beam radiation therapy or brachytherapy. Stem cell transplant may be used to treat kidney cancer.

The methods provided by the invention can provide a beneficial effect for kidney cancer patients, by administration of a nitrobenzamide compound or a combination of administration of a nitrobenzamide compound and surgery, radiation therapy, chemotherapy, immunotherapy and stem cell transplant, or a combination thereof.

Thyroid Cancer

In another aspect, the invention provides methods to treat thyroid cancer. Thyroid cancer is a disease in which cancer (malignant) cells are found in the tissues of the thyroid gland. The four main types of thyroid cancer are papillary, follicular, medullary and anaplastic. Thyroid cancer may be treated by surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy may be external radiation therapy or may required intake of a liquid that contains radioactive iodine. Hormone therapy uses hormones to stop cancer cells from growing. In treating thyroid cancer, hormones can be used to stop the body from making other hormones that might make cancer cells grow.

The methods provided by the invention can provide a beneficial effect for thyroid cancer patients, by administration of a nitrobenzamide compound or a combination of administration of a nitrobenzamide compound and surgery, surgery, radiation therapy, hormone therapy and chemotherapy, or a combination thereof.

AIDS Related Cancers

AIDS-Related Lymphoma

In another aspect, the invention provides methods to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma may occur in AIDS patients, but non-Hodgkin's lymphoma is more common. When a person with AIDS has non-Hodgkin's lymphoma, it is called an AIDS-related lymphoma. Non-Hodgkin's lymphomas may be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used. AIDS-related lymphomas may be treated by chemotherapy, immunotherapy, radiation therapy and high-dose chemotherapy with stem cell transplant. Radiation therapy may be external beam radiation therapy or brachytherapy. AIDS-related lymphomas can be treated by monoclonal antibody therapy.

The methods provided by the invention can provide a beneficial effect for AIDS-related lymphoma patients, by administration of a nitrobenzamide compound or a combination of administration of a nitrobenzamide compound and chemotherapy, radiation therapy and high-dose chemotherapy, or a combination thereof.

Kaposi's Sarcoma

In another aspect, the invention provides methods to treat Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma may occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body. Kaposi's sarcoma may be treated with surgery, chemotherapy, radiation therapy and immunotherapy. External radiation therapy is a common treatment of Kaposi's sarcoma. Some possible surgical options to treat Kaposi's Sarcoma are local excision, electrodeiccation and curettage, and cryotherapy.

The methods provided by the invention can provide a beneficial effect for Kaposi's sarcoma, by administration of a nitrobenzamide compound or a combination of administration of a nitrobenzamide compound and surgery, chemotherapy, radiation therapy and immunotherapy, or a combination thereof.

Viral-Induced Cancers

In another aspect, the invention provides methods to treat viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier.

Virus-Induced Hepatocellular Carcinoma

The causal relationship between both HBV and HCV and hepatocellular carcinoma or liver cancer is established through substantial epidemiologic evidence. Both appear to act via chronic replication in the liver by causing cell death and subsequent regeneration. Different types of treatments are available for patients with liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for virus induce hepatocellular carcinoma patients, by administration of a nitrobenzamide compound or a combination of administration of a nitrobenzamide compound and surgery, radiation therapy, chemotherapy, percutaneous ethanol injection, hyperthemia therapy and immunotherapy, or a combination thereof.

Viral-Induced Adult T cell Leukemia/Lymphoma

The association between HTLV-1 and Adult T cell leukemia (ATL) is firmly established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex.

Adult T cell leukemia is a cancer of the blood and bone marrow. The standard treatments for adult T cell leukemia/lymphoma are radiation therapy, immunotherapy, and chemotherapy. Radiation therapy may be external beam radiation therapy or brachytherapy. Other methods of treating adult T cell leukemia/lymphoma include immunotherapy and high-dose chemotherapy with stem cell transplantion.

The methods provided by the invention can provide a beneficial effect for Adult T cell leukemia patients, by administration of a nitrobenzamide compound or a combination of administration of a nitrobenzamide compound and radiation therapy, chemotherapy, immunotherapy and high-dose chemotherapy with stem cell transplantion, or a combination thereof.

Viral-Induced Cervical Cancer

Infection of the cervix with human papillomavirus (HPV) is the most common cause of cervical cancer. Not all women with HPV infection, however, will develop cervical cancer. Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas. The standard treatments for cervical cancers are surgery, immunotherapy, radiation therapy and chemotherapy. The types of surgery that may be used are conization, total hysterectomy, bilateral salpingo-oophorectomy, radical hysterectomy, pelvic exenteration, cryosurgery, laser surgery and loop electrosurgical excision procedure. Radiation therapy may be external beam radiation therapy or brachytherapy.

The methods provided by the invention can provide a beneficial effect for adult cervical cancer, by administration of a nitrobenzamide compound or a combination of administration of a nitrobenzamide compound and radiation therapy, chemotherapy, or a combination thereof.

CNS Cancers

Brain and spinal cord tumors are abnormal growths of tissue found inside the skull or the bony spinal column, which are the primary components of the central nervous system (CNS). Benign tumors are noncancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors may result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma).

Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumours, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosphamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

The treatments are surgery, radiation therapy, immunotherapy, hyperthermia, gene therapy, chemotherapy, and combination of radiation and chemotherapy. Doctors also may prescribe steroids to reduce the swelling inside the CNS.

The methods provided by the invention can provide a beneficial effect for adult cervical cancer, by administration of a nitrobenzamide compound or a combination of administration of a nitrobenzamide compound and radiation therapy, chemotherapy, or a combination thereof.

PNS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST may be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Muillerian tumor.

The treatments are surgery, radiation therapy, immunotherapy, chemotherapy, and combination of radiation and chemotherapy.

The methods provided by the invention can provide a beneficial effect for PNS cancers, by administration of a nitrobenzamide compound or a combination of administration of a nitrobenzamide compound and radiation therapy, chemotherapy, or a combination thereof.

Oral Cavity and Oropharyngeal Cancer

Management of patients with central nervous system (CNS) cancers remains a formidable task. Cancers such as, hypopharyngeal cancer, laryngeal cancer, nasopharyngeal cancer, oropharyngeal cancer, and the like, have been treated with surgery, immunotherapy, chemotherapy, combination of chemotherapy and radiation therapy. Etoposide and actinomycin D, two commonly used oncology agents that inhibit topoisomerase II, fail to cross the blood-brain barrier in useful amounts.

The methods provided by the invention can provide a beneficial effect for Oral Cavity and Oropharyngeal cancer, by administration of a nitrobenzamide compound or a combination of administration of a nitrobenzamide compound and radiation therapy, chemotherapy, or a combination thereof.

Stomach Cancer

Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

The causes of stomach cancer continue to be debated. A combination of heredity and environment (diet, smoking, etc) are all thought to play a part. Common approaches to the treatment include surgery, immunotherapy, chemotherapy, radiation therapy, combination of chemotherapy and radiation therapy or biological therapy.

The methods provided by the invention can provide a beneficial effect for stomach cancer, by administration of a nitrobenzamide compound or a combination of administration of a nitrobenzamide compound and radiation therapy, chemotherapy, or a combination thereof.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

Common approaches to the treatment include surgery, immunotherapy, chemotherapy, radiation therapy, combination of chemotherapy and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosamide), Velban (vinblastine sulfate) and others may be used.

The methods provided by the invention can provide a beneficial effect for stomach cancer, by administration of a nitrobenzamide compound or a combination of administration of a nitrobenzamide compound and radiation therapy, chemotherapy, or a combination thereof.

Thymus Cancer

The thymus is a small organ located in the upper/front portion of your chest, extending from the base of the throat to the front of the heart, The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

Common approaches to the treatment include surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

The methods provided by the invention can provide a beneficial effect for stomach cancer, by administration of a nitrobenzamide compound or a combination of administration of a nitrobenzamide compound and radiation therapy, chemotherapy, or a combination thereof.

Combination Therapy

One aspect of the invention provides methods for treating cancer using different combinations of treatment regimens. For example, such combinations may include, but are not limited to, the use of one or more of the nitrobenzamide compounds in conjunction with one or more various antineoplastic chemotherapeutic agents, chemopreventative agents, and/or side-effect limiting agents.

Antineoplastic Chemotherapeutic Agents

Suitable antineoplastic chemotherapeutic agents to be used in the present invention include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and antimetastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemeitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the. Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. Administration with such chemopreventative agents in combination with one or more other anticancer agents including the nitrobenzamide compounds can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

Side-effect Limiting Agents

Treatment of cancer with nitrobenzamide compounds alone or in combination with other antineoplastic compounds may be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with the nitrobenzamide compounds and other compounds described herein are also available. For example, see *Goodman & Gilman's The Pharmacological Basis of Therapeutics* 11th ed. Brunton L L, Lazo J S, and Parker K L, ed. McGraw-Hill, New York, 2006.

Formations, Routes of Administration, and Effective Doses

Another aspect of the present invention relates to formulations and routes of administration for pharmaceutical compositions comprising a nitrobenzamide compound. Such pharmaceutical compositions can be used to treat cancer in the methods described in detail above.

The compounds of formula Ia may be provided as a prodrug and/or may be allowed to interconvert to a nitrosobenzamide form in vivo after administration. That is, either the nitrobenzamide form and/or the nitrosobenzamide form, or pharmaceutically acceptable salts may be used in developing a formulation for use in the present invention. Further, in some embodiments, the compound may be used in combination with one or more other compounds or in one or more other forms. For example a formulation may comprise both the nitrobenzamide compound and acid forms in particular proportions, depending on the relative potencies of each and the intended indication. The two forms may be formulated together, in the same dosage unit e.g. in one cream, suppository, tablet, capsule, or packet of powder to be dissolved in a beverage; or each form may be formulated in a separate unit, e.g., two creams, two suppositories, two tablets, two capsules, a tablet and a liquid for dissolving the tablet, a packet of powder and a liquid for dissolving the powder, etc.

In compositions comprising combinations of a nitrobenzamide compound and another active agent can be effective. The two compounds and/or forms of a compound may be formulated together, in the same dosage unit e.g. in one cream, suppository, tablet, capsule, or packet of powder to be dissolved in a beverage; or each form may be formulated in separate units, e.g., two creams, suppositories, tablets, two capsules, a tablet and a liquid for dissolving the tablet, a packet of powder and a liquid for dissolving the powder, etc.

The term "pharmaceutically acceptable salt" means those salts which retain the biological effectiveness and properties of the compounds used in the present invention, and which are not biologically or otherwise undesirable. For example, a pharmaceutically acceptable salt does not interfere with the beneficial effect of the compound of the invention in treating a cancer.

Typical salts are those of the inorganic ions, such as, for example, sodium, potassium, calcium and magnesium ions. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions may contain a nitrobenzamide compound with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., J. Mol. Biol, 23: 238-252 (1965) and Szoka et al., Proc. Natl Acad. Sci 75: 4194-4198 (1978), incorporated herein by reference. Ligands may also be attached to the liposomes to direct these compositions to particular sites of action. Compounds of this invention may also be integrated into foodstuffs, e.g, cream cheese, butter, salad dressing, or ice cream to facilitate solubilization, administration, and/or compliance in certain patient populations.

Pharmaceutical preparations for oral use may be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

For injection, the inhibitors of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton Pa. These compounds may also be formulated for transmucosal administration, buccal administration, for administration by inhalation, for parental administration, for transdermal administration, and rectal administration.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for use in the present invention include compositions wherein the active ingredients are present in an effective amount, i.e., in an amount effective to achieve therapeutic and/or prophylactic benefit in at least one of the cancers described herein. The actual amount effective for a particular application will depend on the condition or conditions being treated, the condition of the subject, the formulation, and the route of administration, as well as other factors known to those of skill in the art. Determination of an effective amount of a nitrobenzamide compound is well within the capabilities of those skilled in the art, in light of the disclosure herein, and will be determined using routine optimization techniques.

EXAMPLES

Example 1

In Vitro Studies—Cytotoxicity Assays

Different types of cancer cell lines of different origin or primary cells were seeded ($5 \times 10^4$) on 48 wells plate, or ($2 \times 10^4$) on 96 wells plate. The cells were cultured in the appropriate medium. Cultures were maintained in a 37° C. incubator in a humidified atmosphere of 95% $O_2$/5% $CO_2$. After the cells were seeded (24 hours), medium was removed and replaced with culture medium in the presence of various concentrations of INO2BA or INH2BP, in the presence or not of 200 μM BSO. After 6 days of incubation at 37° C., cell viability was measured using the Cell Titer-Blue, Cell Viability Assay (Promega) (See O'Brien, J. et al. (2000) Investigation of the Alamar Blue (resazurin) fluorescent dye for the assessment of mammalian cell cytotoxicity. Eur. J. Biochem.267, 5421-26 and Gonzalez, R. J. and Tarloff, J. B. (2001) Evaluation of hepatic subcellular fractions for Alamar Blue and MTT reductase). This assay incorporates a fluorometric/colorometric growth indicator based on detection by vital dye reduction. Cytotoxicity is measured by growth inhibition.

Cytotoxicity was also assessed by counting the number of viable cells. Cells were harvested by washing the monolayer with PBS, followed by a brief incubation in 0.25% trypsin and 0.02% EDTA. The cells were then collected, washed twice by centrifugation and resuspended in PBS. Cell number and viability were determined by staining a small volume of cell suspension with a 0.2% trypan blue saline solution and examining the cells in a hemocytometer. See Kerley-Hamilton et al. (2005) p53-dominant transcriptional response to cisplatin in testicular germ cell tumor-derived human embyronal carcinoma and Cheol et al. (2005) Induction of apoptosis and inhibition of cyclooxygenase-2 expression by N-methyl-N'-nitro-N-nitrosoguanidine in human leukemia cells.

The results of this cell proliferation assay using different cell lines are shown in FIGS. 1-10.

Example 2

Cell Proliferation Measured with BrdU-ELISA

The cells were incubated in the presence of various concentrations of the test substance (drugs) in a black 96-well MP (tissue culture grade; flat, clear bottom) at a final volume of 100 μl/well in a humidified atmosphere at 37° C. 10 μl/well BrdU labeling solution was added if the cells were cultured in 100 μl/well (final concentration: 10 μM BrdU) and the cells were reincubated for additional 2 to 24 hours at 37° C. (if the cells were cultured in 200 μl/well, 20 μl BrdU labeling solution was added). The MP was centrifuged at 300×g for 10 min and the labeling medium was removed with suction using a canulla. The cells were dried using a hair-dryer for about 15 min or, alternatively, at 60° C. for 1 h. 200 μl/well FixDenat was added to the cells and incubated for 30 min at 15-25° C. FixDenat solution was removed thoroughly by flicking off and tapping. 100 μl/well Anti-BrdU-POD working solution was added. This was incubated for approx. 90 min at 15-25° C. Alternatively, this incubation period was varied between 30-120 min, depending on individual requirements. Antibody conjugate was removed by flicking off and wells were rinsed three times with 200- 300 μl/well washing solution. Washing solution was removed by tapping. The clear bottom was sealed with a black adhesive foil and 100 μl/well substrate solution was added to each well with a multi-channel pipette. The light emission of the samples was measured in a microplate luminometer with photomultiplier.

Figure 11:
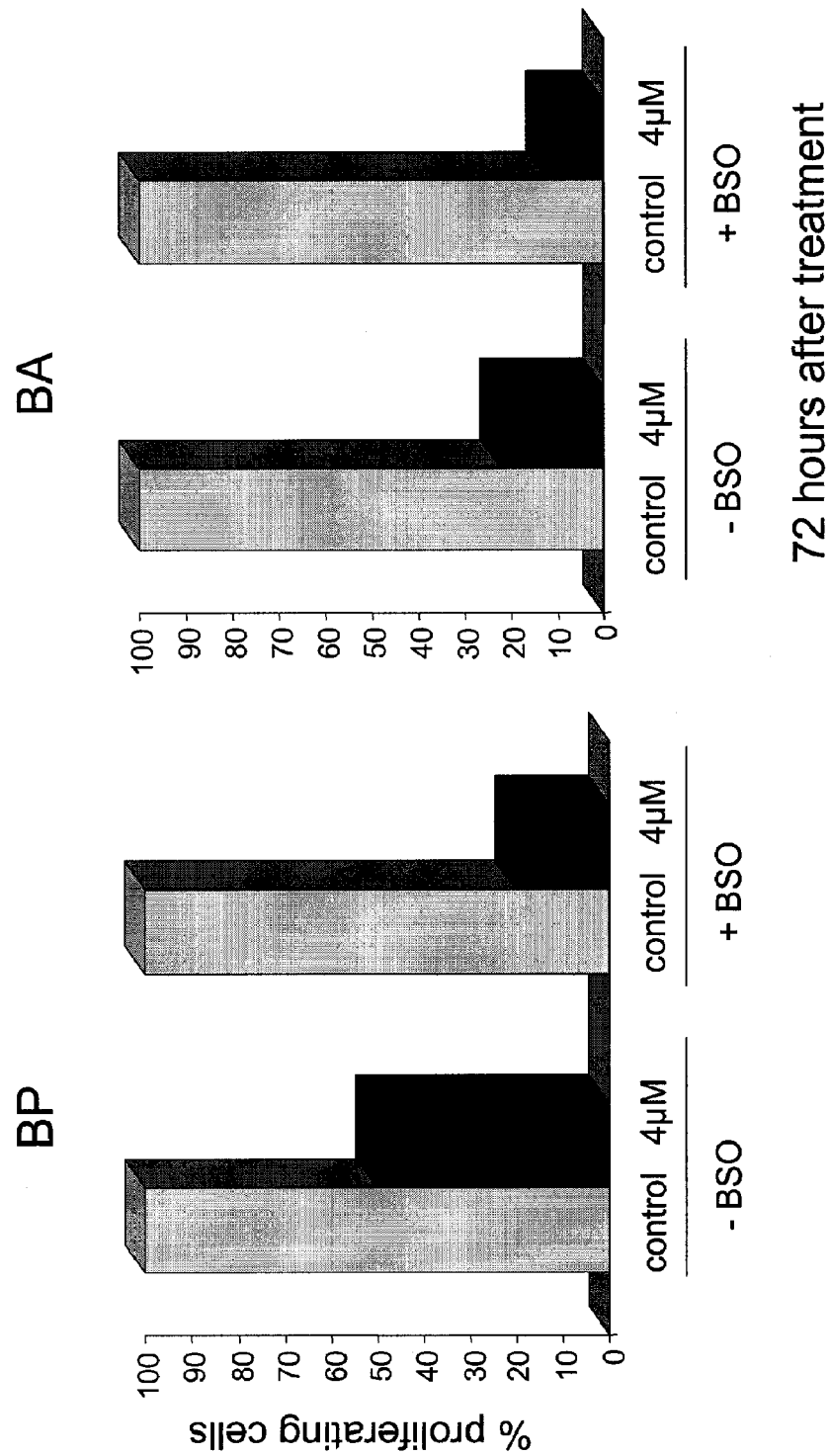
FIG. 11 depicts the effect of nitrobenzamide and benzopyrone compounds on a cervical cancer cell line, with and without the co-treatment of BSO.

The results of this cell proliferation assay using different cell lines and drugs are shown in FIG. 11.

Example 3

| | | Study Design | | |
|---|---|---|---|---|
| Group | Implant conditions | Cells implanted | # Mice | # Tumors needed | Treatment (BID) |
| 1 | sc | $2 \times 10^7$ | 20 | 10 | none |
| 2 | sc | $2 \times 10^7$ | 20 | 10 | Vehicle (10% DMSO in saline) |
| 3 | sc | $2 \times 10^7$ | 20 | 10 | BP + BSO (175 mg/kg + 220 mg/kg) P.O. |
| 4 | sc | $2 \times 10^7$ | 20 | 10 | BA (5 g/kg) I.P. |
| 5 | sc | $2 \times 10^7$ | 20 | 10 | Combo* (30 mg/kg) I.P. and P.O. |

Figure 12:
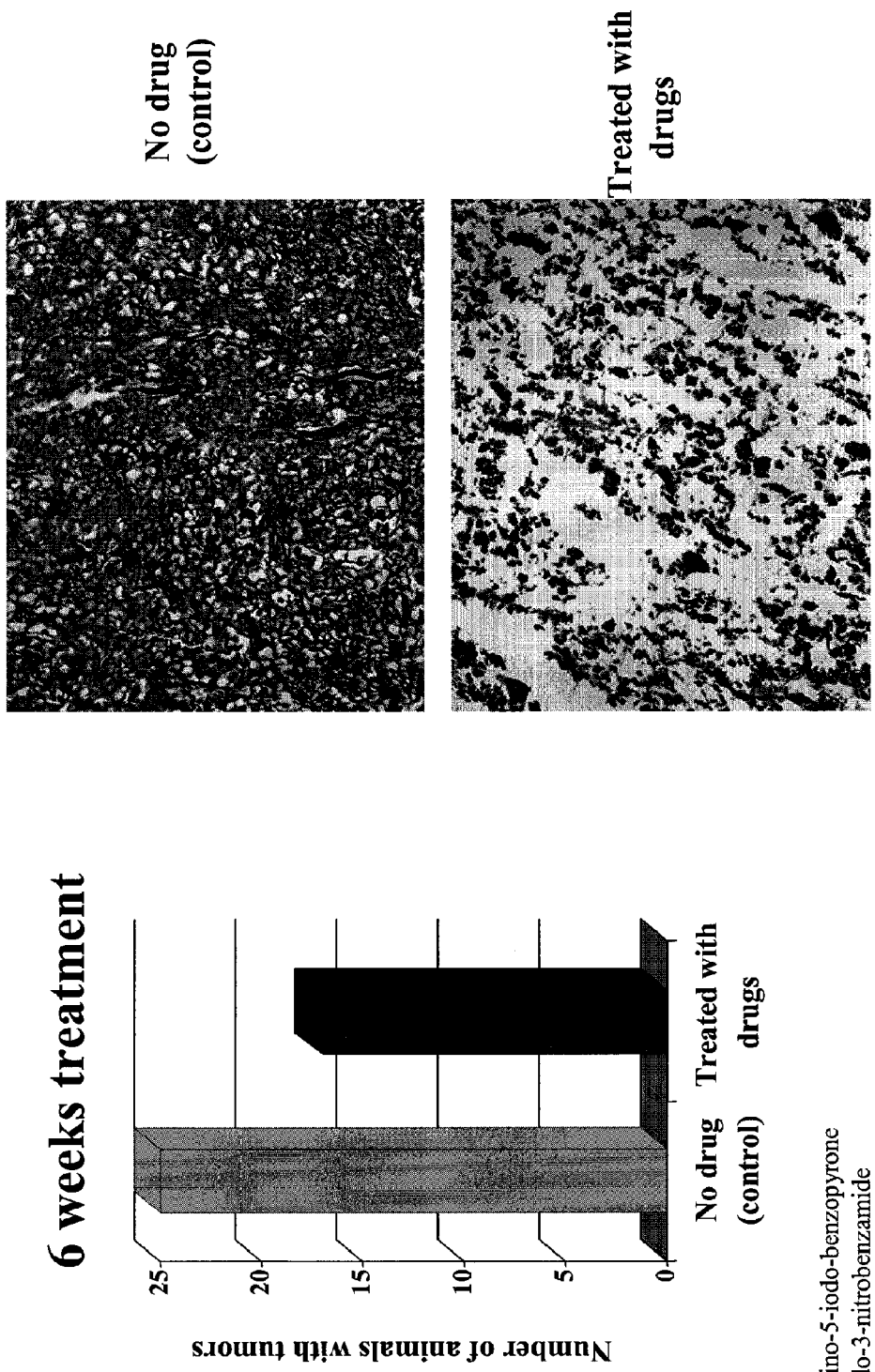
FIG. 12 depicts the effect of nitrobenzamide and benzopyrone compounds on an in vivo subcutaneous breast cancer model, with and without the co-treatment of BSO.

*combination of BP + BSO and BA 100 female NU/NU-nuBR mice (Charles River, 5-6 wks) were implanted with 0.72 mg 17β-estradiol (human) pellets, ear tagged using clips and weighed 24-48 hours prior to tumor cell implantation. Tumor cells, BT474, ($2 \times 10^7$ cells/mouse) were injected into the subscapular mammary fat pad (0.2 ml volume). Caliper measurements began on day 21 and three times weekly thereafter (Mon. Wed, Fri). Animals were segregated according to the presence and absence of tumor and then by tumor volume. Animals were weighed twice weekly beginning the $3^{rd}$ week post implantation (Mon and Fri.). Drug treatment was started when tumor sizes were 150-250 mm$^2$ (L*W*H). Drug and vehicle administration was BID by gavage (BP+BSO) and SID by IP (BA) for five days. There was a two day rest period before the next cycle began. It was planned that animals received three cycles (5 days each) unless there was unexpected toxicity. Body weight loss that exceeded 15% of initial values or display of certain symptoms was criteria for animal euthanasia. Drug was administered by gavage and IP in volume of 5 ml/kg. Drug and vehicle were stored at 4° C. in foil-covered bottle. Results of this experiment are shown in FIG. 12.

Example 4

The effects of the compounds were evaluated on ovarian human cancer cells (OVCAR) xenografts in nude mice.

Female NU/NU 37-BU-04-BAC mice (Charles River, 5-6 weeks) were ear tagged using clips and weighed 24-48 hours prior to tumor cell implantation. Tumor cells Ovcar3 ($5 \times 10^6$ cells/mouse) were implanted subcutaneously into the subcapular mammary fat pad of female nude mice hosts. Caliper measurement began on day 7 post tumor cells implantation and 2 times weekly thereafter (Mon and Fri). Animals were segregated according to the presence or absence of tumor and then tumor volume. Animals were weighed once a week. Drug treatment started when sizes were 0.4-0.5 cm in largest diameter. 4-Iodo-3-nitrobenzamide (BA) (in 50 μl of 100% DMSO/mouse and vehicle (50 μl of 100% DMSO/mouse) were injected by IP twice per day for five days. There was a two days rest period before the next cycle began.

| | STUDY DESIGN | | |
|---|---|---|---|
| Group | Implant conditions | Cells implanted | TREATMENT |
| 1 | SC | $5 \times 10^6$ | Vehicle × 2 (50 μl of 100% DMSO/mouse) |
| 2 | SC | $5 \times 10^6$ | BA 25 mg/kg × 2/day (in 50 μl of 100% DMSO/mouse) |
| 3 | SC | $5 \times 10^6$ | BA 50 mg/kg × 2/day (in 50 μl of 100% DMSO/mouse) |
| 4 | SC | $5 \times 10^6$ | Nothing (Control) |

Figure 13:
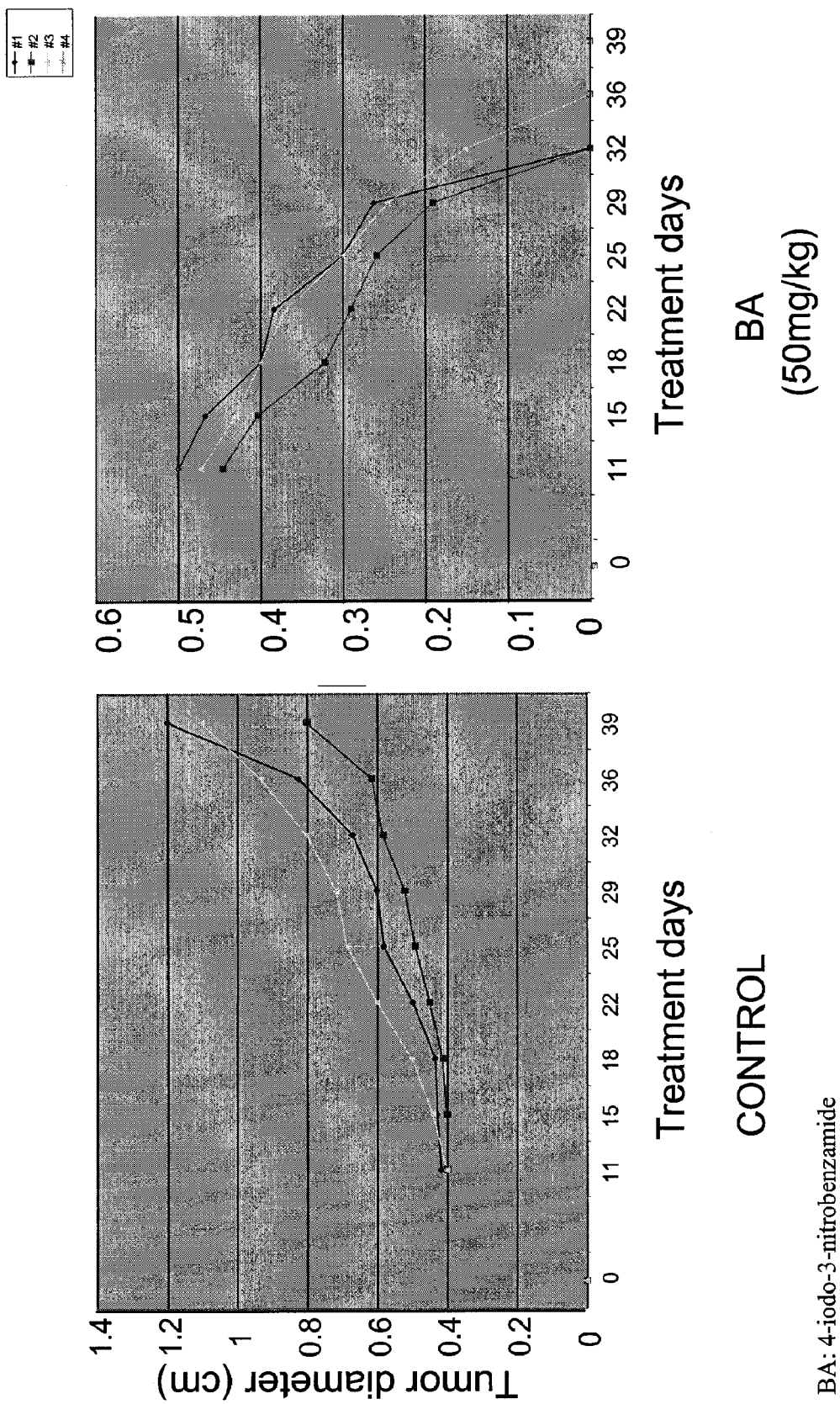
FIG. 13 depicts the effect of 4-Iodo-3-nitrobenzamide in OVCAR3 (human ovarian adenocarcinoma) xenograft model in nude mice.
Figure 14A:
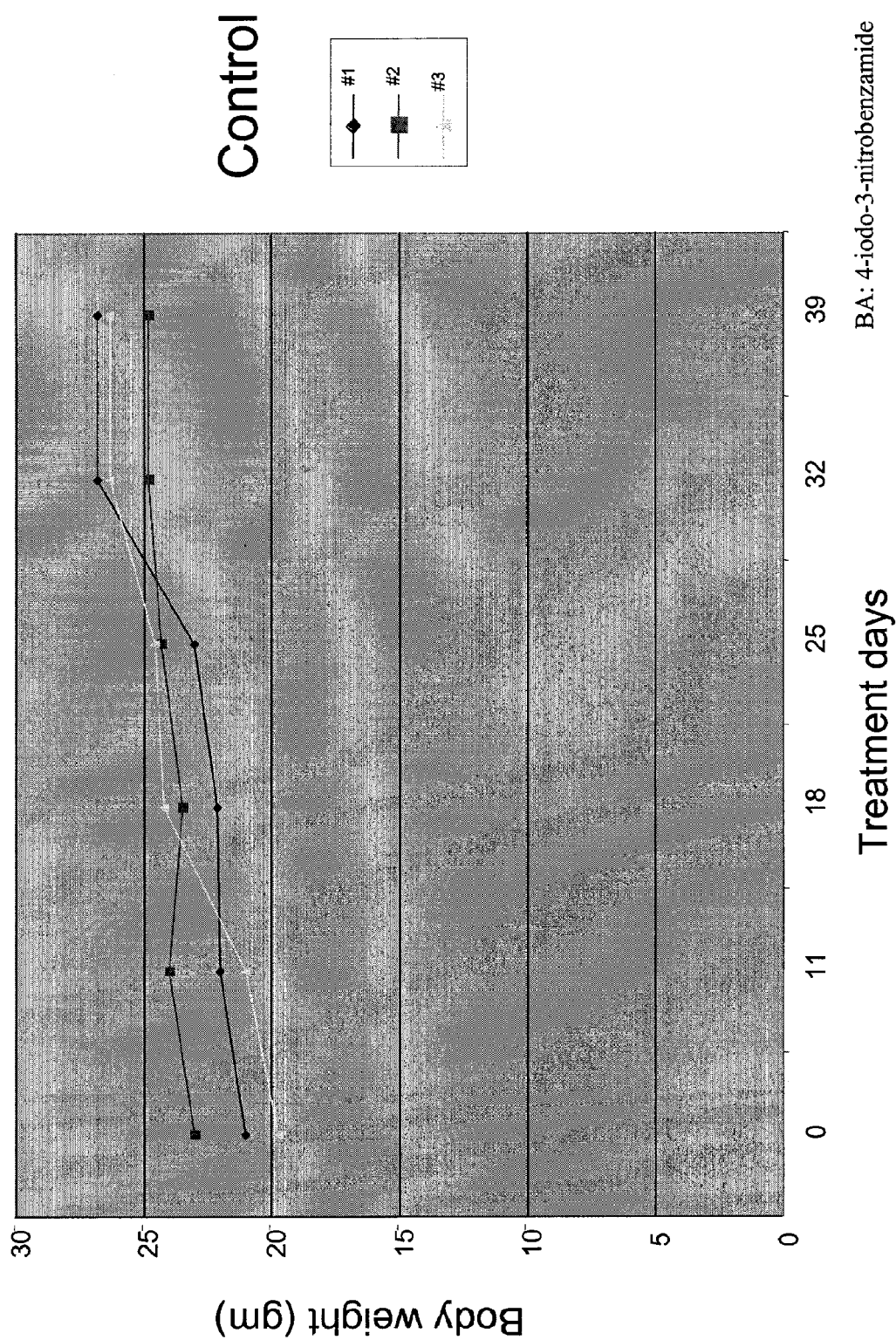
FIG. 14 depicts the effect on body weight during the evaluation of 4-Iodo-3-nitrobenzamide in OVCAR3 (human ovarian adenocarcinoma) xenograft model in nude mice.
Figure 14B:
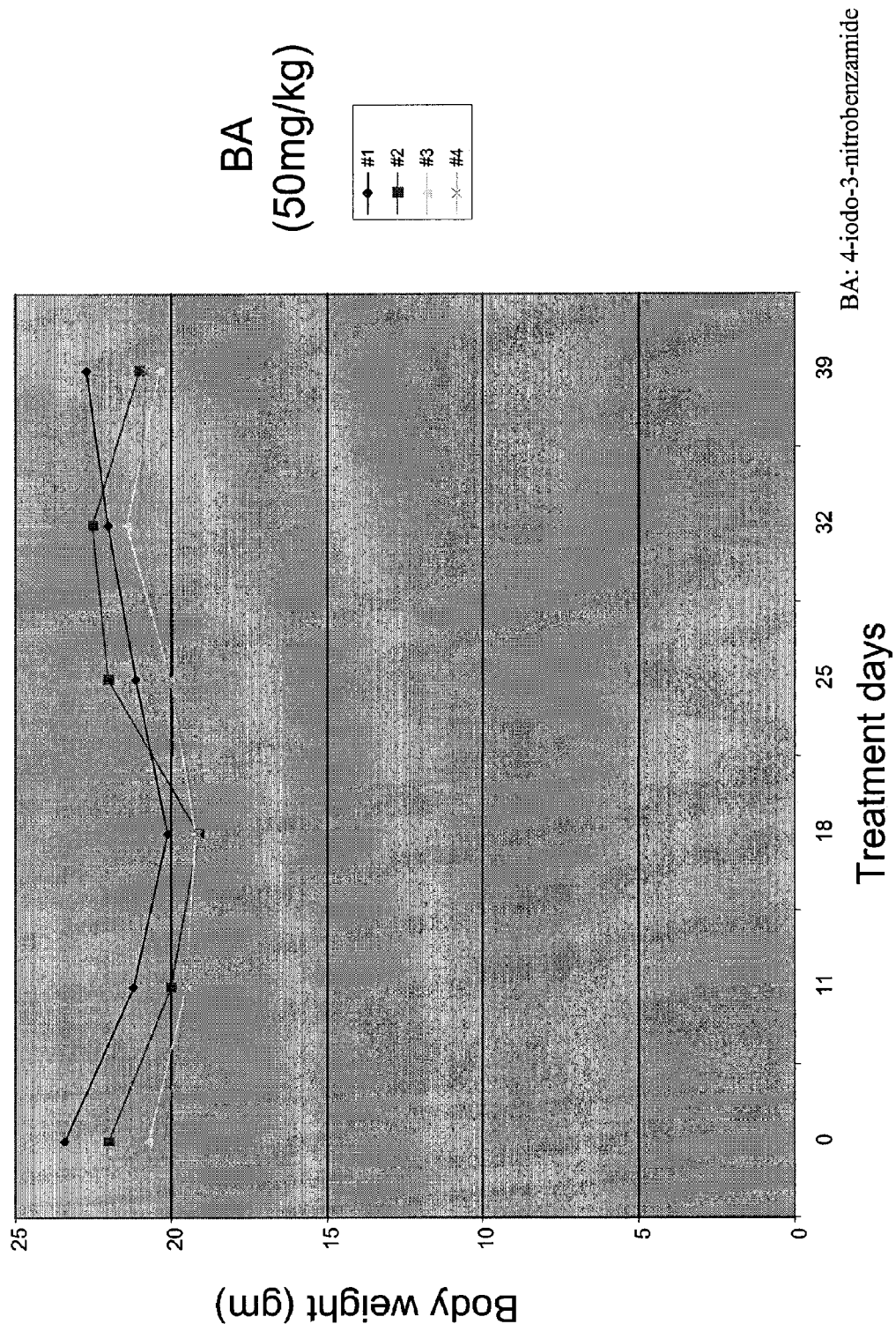

Results of the experiments are shown in FIGS. 13 and 14.

Example 5

The objective of this study was to evaluate the efficacy of the coumarin analog 6-amino-5-iodo-2H-1-benzopyran-2-one (BP) in mammary (MDA MB 231) cancer nude mouse xenografts.

Tumor-bearing female mice were treated 5 days a week, Monday through Friday, with BP (two dose levels). The study was divided into two tasks: Task 1 was to test the effect of pretreating the animals with BP prior to tumor implantation, and Task 2 was to test the effect of initiating treatment after tumors had formed. For Task 1, female nude mice were pretreated with BP (either 300 or 1000 mg/kg) for one week, tumor cells were then implanted subcutaneously, and treatment continued for 4-8 weeks with oral doses of either corn oil:PEG 400 or BP. In Task 2, BP was compared to chemotherapeutic agents used clinically. Female nude mice bearing tumors of 20-30 mm3 (MDA MB 231) were treated five times a week with oral doses of either corn oil:PEG 400, BP, or cyclophosphamide (CTX, positive control for MDA MB 231). Treatment for the MDA MB 231 tumors was continued until the tumors of each animal reached ≧1600 mm$^3$ or ulcerated. Some MDA MB 231 tumors in Task 2 did not reach 1600 mm$^3$. Follow-up of regressed tumors continued for 3 months.

The MDA MB 231 mammary tumors responded to treatment with BP and CTX (positive control). In Task 1, BP at 300 mg/kg and 1000 mg/kg appeared to prevent tumor formation in 2/9 animals and 2/10 animals, respectively. All 8 control animals formed tumors. In Task 2, treatment of animals with BP (1000 mg/kg or 2000 mg/kg body weight) resulted in regression of 3/5 tumors.

General Methods

MDA MB 231 human mammary cancer cells were injected subcutaneously into the right flank of female nude mice. For Task 1, BP was administered for 5 consecutive days prior to tumor cell implantation, and drug administration continued 5 days a week for 4-8 weeks thereafter. For Task 2, cancer cells were injected when the tumors reached a mean tumor volume of 50-60 mm$^3$, and mice were divided into groups of eight and treated with corn oil:PEG 400 (control), BP, or CTX (MDA MB 231 positive control). Tumor volumes were monitored for 90 days (for MDA MB 231) after the beginning of treatment.

Experimental Procedures

Cell Lines

MDA MB 231 is a human mammary cancer cell line that was established in 1973 from a pleural effusion of a patient who had been treated with 5-FU, doxorubicin, methotrexate, and CTX in the 3 months before the cell line was initiated. This line is estrogen receptor negative and has been used in screening anticancer drugs that are not targeted as hormone antagonists. MDA MB 231 was grown in Dulbecco's modified Eagle medium (DMEM) with 1.5 g NaHCO$_3$/L, 10% fetal bovine serum (FBS), and 2 mM L-glutamine and was kept at 37° C. in a humidified 5% CO$_2$/air incubator. Antibiotics were not added to the medium.

Animal Tumor Model

Swiss NCr nude (nu/nu) female mice, age 4-5 weeks, were purchased from Taconic (Germantown, N.Y.). The animals were housed three per cage in sterile filter-topped cages in a barrier clean room purchased from Bio Bubble, Inc. (Fort Collins, Colo.). Upon arrival, they were quarantined for four working days before use. Temperature was maintained at 72±5° F. and relative humidity at 35-70%, and a 12-hr light/dark cycle was used. The mice were fed sterile, autoclavable, certified Purina rodent chow ad libitum. Drinking water was acidified and autoclaved, and the source water was recirculated, deionized, UV-treated, and 5 µm filtered.

After the animals were released from quarantine, the mice were injected subcutaneously in the right flank with 1 or 5×10$^6$ MDA MB 231 cells (0.1-ml injection volume). The mice for Task 1 received pretreatment for 5 days before cell injection. Tumor dimensions and body weight were measured twice weekly. Vernier calipers were used to measure tumors in three planes, and tumor volume (V) was calculated as follows: $V=\pi(x \times y \times z)/6$, where x, y, and z were the tumor measurements minus skin thickness. At the end of the experiment, the mice were sacrificed by CO$_2$ inhalation followed by cervical dislocation.

Pharmaceuticals

BP was made up in corn oil:PEG 400 (2:1, V/V) at concentrations of 30 mg/ml and 100 mg/ml. The drug was a suspension at these concentrations. Positive control drugs were made up on phosphate buffered saline (PBS) and CTX at 15 mg/ml. Both drugs were filter-sterilized (0.2-µm filter) before use.

Treatment Protocol

For Task 1, mice to be implanted with MDA MB 231 tumor cells were pretreated for 5 days with BP (300 or 1000 mg/kg), and following subcutaneous injection of the cell suspension, drug treatment was continued 5 days a week (Monday through Friday) for a minimum of 4 weeks.

For Task 2, after the tumor volumes reached a predetermined size (mean tumor volume 50-60 mm$^3$), mice were divided into treatment groups of eight mice each. All treatments of BP were administered five times per week (Monday through Friday) for at least 4 weeks. CTX was administered intraperitoneally one time only at a dose of 150 mg/kg. All BP treatments were administered orally; the dosage was 1000 or 2000 mg/kg for those implanted with MDA MB 231 cells. For each task, all treatments began on the same day.

The tumors were measured twice weekly for at least 9 weeks (MDA MB 231) after the first treatment. The mean tumor volume for each group was calculated for each time point. Comparisons between groups at specific times were made using an unpaired, two-tailed t-test, and the results were analyzed using analysis of variance (ANOVA). For Task 2, individual tumor volumes (V) were expressed as a fraction of the tumor volume on Day 0, the first day of treatment ($V_0$). For each group, the mean of the ratio $V/V_0$ was plotted as a function of time after treatment. Response to treatment was measured in two ways, depending on the tumor response to treatment. The tumor volume doubling time (VDT) and volume quadrupling time (VQT) were determined for each tumor by linear regressions on the plot of time as a function of log (tumor volume) in groups where there was a response to treatment. Tumor growth delay for each treatment group was determined and comparisons between groups were analyzed using ANOVA.

Systemic toxicity was assessed from reductions in body weight after treatment. The mice were sacrificed at the end of the follow-up period, or earlier in their tumor volumes reached 1600 mm$^3$ or the tumors ulcerated.

Statistical Analysis

Statistical analysis as described above was performed using InStat (Graphpad Software, San Diego, Calif.).

Tumor Growth

MDA MB 231 tumors were measurable within 3 weeks of tumor cell injection and grew more slowly, with a doubling time of 7 days. These values were calculated from the control group. Mean tumor volumes and body weights at the start of treatment are shown in Table 1 for Task 1 and Table 2 for Task 2.

TABLE 1

MOUSE PARAMETERS AT THE START OF TREATMENT - TASK 1

| Treatment Group | Tumor Volume (mm$^3$ ± SEM*) | Mouse Weight (g ± SEM*) |
| --- | --- | --- |
| PBS (control) MDA MB 231 | 0 | 24.0 ± 0.8 |
| 300 mg/kg | 0 | 24.6 ± 0.9 |
| 1000 mg/kg | 0 | 23.6 ± 07 |

*SEM = Standard error of the mean.

TABLE 2

MOUSE PARAMETERS AT THE START OF TREATMENT - TASK 2

| Treatment Group | Tumor Volume ($mm^3 \pm SEM^*$) | Mouse Weight ($g \pm SEM^*$) |
| --- | --- | --- |
| MDA MB 231 | | |
| Corn oil (control) | 19.1 ± 5.1 | 24.4 ± 0.54 |
| 1000 mg/kg | 24.4 ± 5.8 | 24.5 ± 0.7 |
| 2000 mg/kg | 23.5 ± 5.8 | 23.0 ± 0.8 |
| CTX, 150 mg/kg | 24.0 ± 4.4 | 23.8 ± 0.4 |

*SEM = Standard error of the mean

Tumor Response to Treatment

Pretreatment of mice implanted with MDA MB 231 resulted in prevention of tumor formation in 1/9 mice and regression of one small tumor which grew to a size of 10 mm$^3$ before disappearing. Pretreatment of mice with 1000 mg/kg BP prevented tumor growth in 2/10 animals (20%), and one tumor which grew to a size of 195 mm$^3$ by Day 63 had regressed to 93 mm$^3$ by Day 86, when the study was ended. The mean survival time of animals pretreated with 1000 mg/kg BP was 115 days, compared with 72 days in the control group (p=0.01), if we assume that animals which did not form tumors survived 6 months (180 days).

The MDA MB 231 tumors in Task 2 responded to both treatments. CTX (150 mg/kg) and BP (1000 or 2000 mg) slowed tumor growth substantially, and treatment induced complete regressions with both drugs. Two animals treated with 1000 mg/kg BP showed no reduction in growth rate of the tumors compared with the controls, whereas of the 2 of the tumors regressed completely. Tumors implanted in all three of the animals in the 2000 mg/kg BP treatment group regressed. Treatment was stopped on Day 42, when 2 of the tumors had completely regressed, and one relatively large tumor had started to regress (310 mm$^3$ on Day 31 to 163 mm$^3$ on Day 45). None of the tumors which had completely regressed started to regrow during the 3 month follow-up period, however the tumor which had partially regressed began to regrow after treatment was stopped and had reached a size of 1835 mm$^3$ at the time the experiment was terminated. There was a trend toward increased survival time in animals treated with 2000 mg/kg BP.

Figure 15:
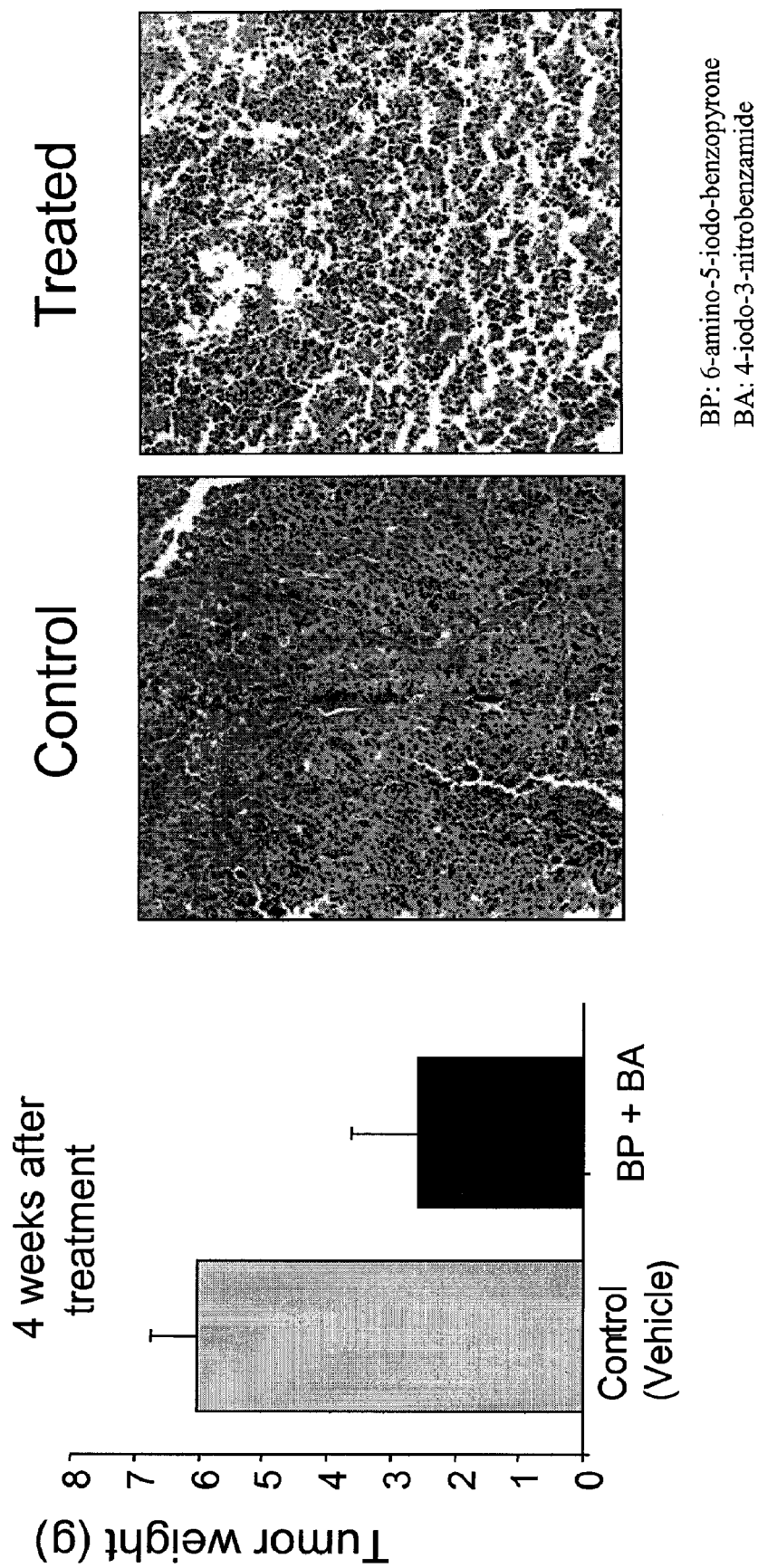
FIG. 15 depicts the effect of 6-amino-5-iodo-2H-1-benzopyran-2-one (BP) in mammary (MDA MB 231) cancer nude mouse xenografts.
Figure 16:
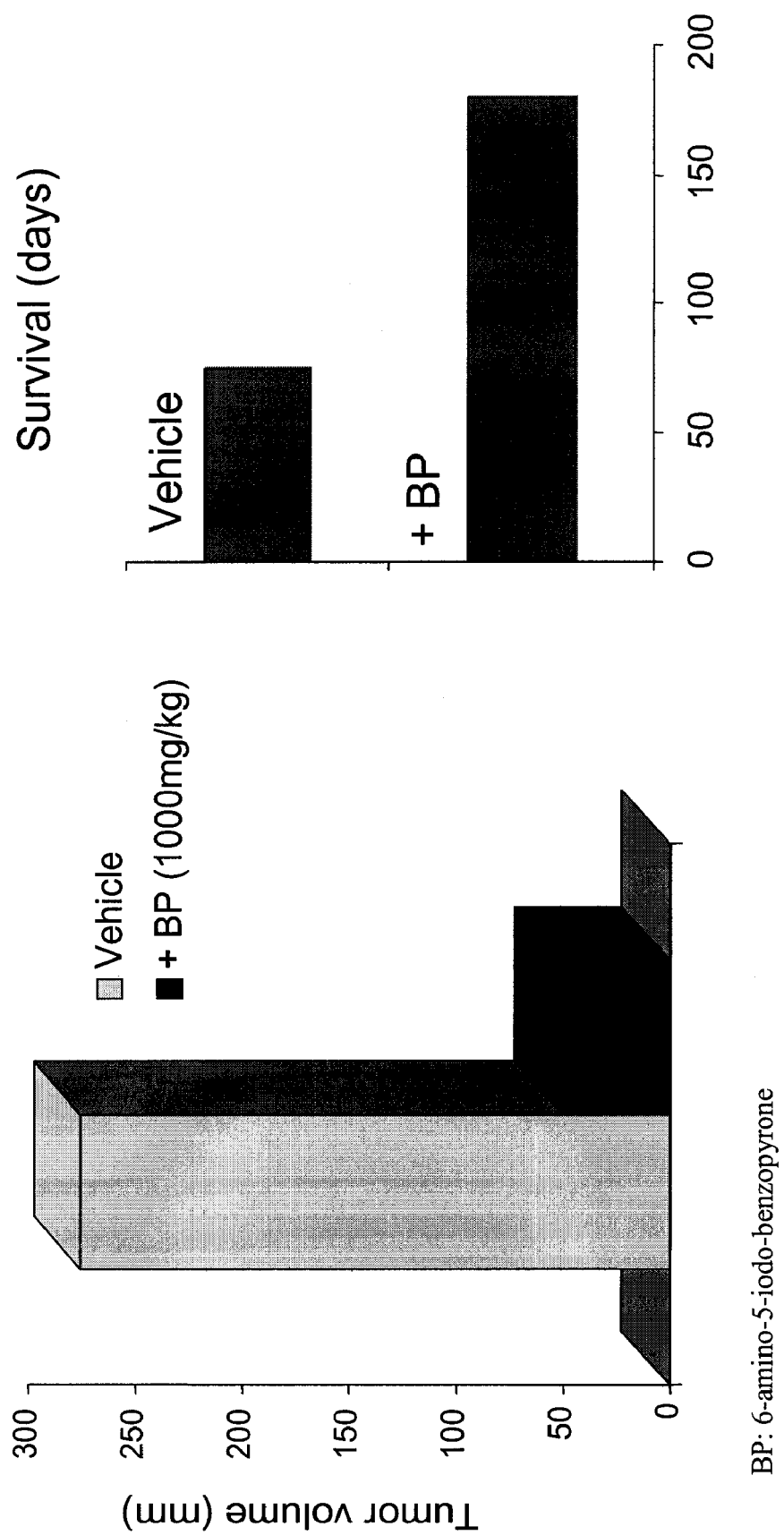
FIG. 16 depicts the effect of 6-amino-5-iodo-2H-1-benzopyran-2-one (BP) and 4-Iodo-3-nitrobenzamid (BA) in mammary (MDA MB 231) cancer nude mouse xenografts.

Results of the experiments are shown in FIGS. 15 and 16.

Example 6

Nonclinical Toxicology

The nonclinical toxicology program supporting the oncology application with 4-iodo-3-nitrobenzamide (BA) consisted of acute (single-dose), two-week (multiple-dose), dose-range, and multiple-dose (4-week) toxicology studies conducted in rats and dogs in which BA was administered intravenously. These studies used BA formulated in beta-hydroxypropylcyclodextrin (25%) (Kleptose).

The definitive 4-week studies involved the twice-weekly administration of BA at doses as great as 60 mg/kg/day and included comprehensive clinical evaluations and/or the microscopic assessment of a full list of tissues. The multiple-dose dog study included electrocardiographic measurements and physical examinations including heart rate, respiratory rate, and body temperature evaluations. Toxicokinetic data also was collected in the 4-week multiple-dose rat and dog studies. In addition, two special studies were conducted, an in vitro hemolytic potential/plasma compatibility study with dog and human blood and plasma and an IV local tolerance study in the rabbit. A single-dose investigative study was also conducted in rats to assess the influence of dosing rate upon BA-induced neurobehavioral effects in this model.

BA was well tolerated following single intravenous doses as great as 50 mg/kg in rats and dogs. Following single-bolus intravenous doses of 100 mg/kg, clinical signs, including convulsions in rats and ataxia in dogs, were noted. Repeat doses of 100 mg/kg in dogs caused clinical changes that consisted primarily of excessive salivation and reductions in body weight and food consumption.

Example 7

Title: A Phase 1, first in human, open-label, dose escalation study evaluating the safety and pharmacokinetics of BA in subjects with advanced solid tumors.

Study Phase: 1

Indication: Treatment of advanced solid tumors

Primary Objective: To assess the safety, establish the maximum tolerated dose (MTD) and generate pharmacokinetic profiles of BA after IV administration in adult subjects with histologically documented advanced solid tumors that are refractory to standard therapy or for which no standard therapy is available.

Secondary Objective(s): To evaluate the response in study subjects (per RECIST criteria) with measurable disease. To assess safety profiles: significant laboratory changes and adverse events (AEs) not defined as a dose limiting toxicity (DLT).

Exploratory Objective(s): To assess the effect of treatment on biological markers of tumor status.

Study Design: A phase 1, first in human, open-label, sequential dose escalation study designed to determine safety, MTD and PK profile of BA. BA will be administered intravenously twice weekly (days 1 and 4 of each week) for 3 weeks, followed by a one week BA treatment free period per one 28-day cycle. Cycle one (day 1 thru day 28) will be defined as the safety phase of the study during which the MTD will be determined. The remainder of the study will be termed the maintenance phase. Subjects may participate in this study until a subject experiences a drug intolerance or disease progression.

Safety assessment will follow the guidelines provided in the Cancer Therapy Evaluation Program Common Terminology Criteria for Adverse Events (CTCAE) Version 3.0 dated December, 2003. The first assessment of tumor response, for measurable disease, will be performed during week 8 of the study, and approximately every 8 weeks thereafter. The modified Response Evaluation Criteria in Solid Tumors (RECIST) criteria will be used to establish disease progression. For non-measurable disease, best medical practices will be used to determine time of disease progression Primary Endpoint and Secondary Endpoints: Primary endpoints being safety/tolerability to characterize DLT and PK profiles: BA half life (t½), maximum observed concentration (Cmax), area under the plasma concentration-time curve (AUC), and clearance (CL). Secondary endpoints being tumor response per RECIST criteria; safety profiles: significant laboratory changes and other AEs (not defined as a DLT). Exploratory being reduction in circulating tumor cell (CTC) levels.

Sample Size: As many as 36 subjects are expected to participate in this study. Study subjects will be assigned to sequential cohorts of 1, 3, or 6 subjects at varying dose levels. As many as 10 dose cohorts may be needed to define the MTD.

Summary of Subject Eligibility Criteria:

Inclusion criteria include: (a) ≧18 years old with a pathologically documented, advanced solid tumor that is refractory to standard treatment or for which no standard therapy is available, (b) Eastern Oncology Cooperative Group (ECOG)

performance status of ≦2, and (c) absolute neutrophil count (ANC) ≧1.5×109/L (without GCF support within 2 weeks of study day 1); platelet count ≧100.0×109/L (without transfusion within 2 weeks of study day 1); and hemoglobin ≧9.0 g/dL (erythropoietic agents allowed).

Exclusion Criteria include: subject enrolled in another investigational device or drug trial, or is receiving other investigational agents; hematological malignancies; symptomatic or untreated brain metastases requiring concurrent treatment, inclusive of but not limited to surgery, radiation, and corticosteroids; history of seizure disorder; MI within 6 months of study day 1, unstable angina, congestive heart failure (CHF) with New York Heart Association (NYHA)>class II, uncontrolled hypertension; concurrent or prior (within 7 days of study day 1) anticoagulation therapy; specified concomitant medications (see Section 4.2.3); serum creatinine >1.5×ULN; elevated liver enzymes (AST/ALT)>2.5×ULN, or >5.0 if secondary to liver metastases, alkaline phosphatase>2.5×ULN or >5.0 if secondary to liver or bone metastases; total bilirubin>1.5×ULN; systemic chemotherapy within 28 days of study day 1 (42 day washout period for BCNU or mitomycin C); radiation therapy within 28 days of study day 1; antibody therapy for the treatment of an underlying malignancy within 1 month of study day 1, and; concurrent chemotherapy with any agent other than BA or radiation therapy is not permitted throughout the course of the study.

Investigational Product Dosage and Administration: BA will be provided in 10 mL vials of 10 mg/mL concentration. t is estimated that as many as 10 subject cohorts may be necessary to determine the MTD.

Starting Dose (Cohort A): In cohort A, a single subject will receive BA twice weekly at a dose level of 0.5 mg/kg based on weight measured at screening. If this subject experiences a grade 2 toxicity or higher, then 3 additional subjects will be enrolled in this cohort. If no additional subjects dosed in this cohort experience a DLT, then dose escalation will occur as below. If no DLT occurs in the initial subject, dose escalation will occur as below.

Dose Escalation Prior to Grade 2 Toxicity (Potential Cohorts B-J): Until a subject experiences a grade 2 toxicity or higher, one subject will be initially enrolled in all subsequent cohorts at planned 100% dose level increases, with possible cohort expansion as described for cohort A. Safety data will be reviewed after 6 doses of BA, and a decision to escalate to the next cohort will be made if no subject experiences a grade 2 toxicity or higher. If 1 subject in this cohort experiences a grade 2 toxicity or higher, then 3 additional subjects will be enrolled in this cohort. If none of these three additional subjects dosed in this cohort experience a DLT, then further dose escalation will occur. If 1 of 3 subjects experience a DLT, then 3 additional subjects will be enrolled in the same cohort with the same dose. If 0 of these 3 subjects experience a DLT then escalation will occur. If one or more of the additional subjects in a cohort experience a DLT, then the previous lower dose level will be defined as the MTD. Additional subjects may be accrued at the MTD if needed to ensure at least 18 subjects receive BA in the study.

Dose Escalation After Grade 2 Toxicity Level (Potential Cohorts B-J): After the dose associated with the initial grade 2 toxicity is expanded and cleared for dose escalation to the next level, then three subjects will be initially enrolled in all future cohorts (cohorts B, C, D, E, F, G, H, I, or J). If 0 of the 3 initial subjects experience a DLT, then dose escalation to the next cohort will proceed. If 1 of 3 subjects experience a DLT, then 3 additional subjects will be enrolled in the same cohort with the same dose. If 0 of these 3 subjects experience a DLT, then escalation will occur. If one or more of the additional subjects in a cohort experience a DLT, then the previous lower dose level will be defined as the MTD. Additional subjects may be accrued at the MTD if needed to ensure that at least 18 subjects receive BA in the study.

Intra-subject Dose Escalation: Once a BA dose level has been declared safe and tolerable based on the criteria defined above all subjects currently on lower doses may be escalated to the highest safe dose as appropriate (determined by the principal investigator). Once a MTD is determined, all subjects in the study may be escalated as appropriate to receive the MTD.

Overall Dose Escalation Limitations: When a grade 2 toxicity has been observed and that dose level subsequently cleared, individual dose escalations between cohorts will be more conservative, and will be limited to approximately a maximum 40% increase from the previous dose level until a grade 3 toxicity is seen, with subsequent escalations limited to approximately 25% dose increases. Absolute dose escalation will be decided by the safety review group after review of all available data.

Control Group: None

Procedures:

Screening: Pre-enrollment screening tests and evaluation will be performed only after a signed, written Institutional Review Board (IRB) approved informed consent is obtained from each subject. Procedures will be performed within 2 weeks of study day 1 unless otherwise noted. Clinical evaluation includes complete history, physical examination, ECOG status, height, weight, vital signs, and documentation of concomitant medications. Laboratory studies include hematology (with differential, reticulocyte count, and platelets); prothrombin time (PT) and partial thromboplastin time (PTT); comprehensive chemistry panel (sodium, potassium, chloride, CO2, creatinine, calcium, phosphorous, magnesium, BUN, uric acid, albumin, AST, ALT, alkaline phosphatase, total bilirubin, and cholesterol, HDL, and LDL), urinalysis with microscopic examination, serum tumor markers, serum or urine pregnancy test for women of child bearing potential. Cardiac studies include creatine kinase (CK), and 12-lead electrocardiogram (EKG). Clinical staging includes imaging for measurable disease by computed tomography (CT) or magnetic resonance (MRI) within 4 weeks of study day 1. Documentation of clinical staging for non-measurable disease will occur.

Treatment: Eligible subjects will be enrolled into the study and receive study drug on Day 1. Pre-dose and post-dose tests will be performed as outlined in the study protocol. Dosing of BA will occur twice weekly at days 1, 4, 8, 11, 15, and 18 of each 28 day cycle; and administered over an infusion period as long as 2 hours. On day 29, subjects will start cycle 2 and resume dosing at days 1, 4, 8, 11, 15, and 18 of that and each subsequent cycle. Subjects may participate in this study until they experience a drug intolerance or disease progression or withdraw consent. Subjects meeting the modified RECIST criteria of disease progression may continue in the study if they are demonstrating clinical benefit.

The first scheduled tumor response measurement for measurable disease will be performed during week 8 (study day 50±5 days) of the study, and every 8 weeks thereafter. Tumor response according to the modified Response Evaluation Criteria in Solid Tumors (RECIST) criteria will be used to establish disease progression by CT or MRI (the same technique used during screening must be used). For non-measurable disease, best medical practices will be used to determine time of disease progression.

End of Study: All subjects should have the end of study procedures as described in the protocol completed no more than 30 days after the last dose of BA. Additionally, subjects will have overall tumor response assessed via clinical imaging if not done within 30 days prior to the last dose of BA.

Statistical Considerations: Descriptive statistics will be calculated for safety, PK, and PD endpoints. Response data, to establish time to progression, will be reported descriptively in the form of listings. Tumor progression data will be categorized using the modified RECIST criteria.

PK parameters will be estimated using non-compartmental methods. PK parameters will be summarized by the arithmetic mean, standard deviation, coefficient of variation, maximum, minimum, median, and geometric mean. Summary statistics will be calculated with SPlus version 5.1 (or later).

If appropriate, data may also be analyzed by a non-linear mixed-effects modeling approach (population approach) to compartmental analysis. Other analyses will be done descriptively as appropriate.

Results will be analyzed after all subjects have received at least one cycle (6 doses) of BA at the MTD dose level (or their highest dose level received in the study). This will coincide with the completion of the safety phase of the study. Additional analyses will be performed on an ongoing basis as necessary to provide information for design of future trials.

The above examples are in no way intended to limit the scope of the instant invention. Further, it can be appreciated to one of ordinary skill in the art that many changes and modifications can be made thereto without departing from the spirit or scope of the appended claims, and such changes and modifications are contemplated within the scope of the instant invention.

It will be apparent to one of ordinary skill in the art that many changes and modifications can be made thereto without departing from the spirit or scope of the appended claims.

The invention claimed is:

1. A method of treating a cancer comprising administering to a subject in need thereof an effective amount of a composition comprising a compound of formula

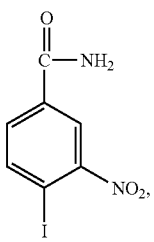

, and pharmaceutically acceptable salts thereof,
wherein said cancer is selected from the group consisting of a ovarian cancer, endometrium cancer, cervical cancer, pancreatic cancer, central nervous system cancer a glioma, and a lung cancer.

2. A method of treating a cancer comprising administering to a subject in need thereof an effective amount of a composition comprising a compound of formula

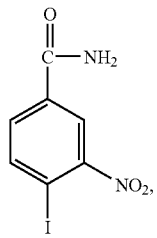

, and pharmaceutically acceptable salts thereof,
wherein said cancer is selected from the group consisting of an ovarian adenocarcinoma, an ovarian adenocarcinoma that has migrated into the abdominal cavity, an epithelioid carcinoma in a pancreatic duct, an adenocarcinoma in a pancreatic duct, an adenocarcinoma in the cervical epithelium, and a lung cancer.

3. The method of claim 1 or 2, further comprising surgery, radiation therapy, chemotherapy, gene therapy, immunotherapy, or a combination thereof.

4. The method of any of claim 1 or 2, further comprising administering an effective amount of buthionine sulfoximine.

5. The method of claim 1 or 2, wherein said administration is intravenous.

6. The method of claim 1 or 2, wherein a poly-ADP-ribose polymerase (PARP) molecule is inhibited by said compound in said subject.

7. The method of claim 1 or 2, wherein a tumor cell undergoes apoptosis, cell cycle arrest, and/or necrosis in said subject.

8. The method of claim 1 or 2, further comprising administering an effective amount of a benzopyrone compound of formula (II):

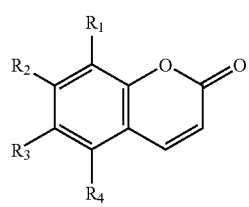

Formula II wherein $R_1$, $R_2$, $R_3$ and $R_4$ are independently selected from the group consisting of H, halogen, optionally substituted hydroxy, optionally substituted amine, optionally substituted lower alkyl, optionally substituted phenyl and optionally substituted $C_3$-$C_8$ cycloalkyl or a salt thereof.

* * * * *

UNITED STATES PATENT AND TRADEMARK OFFICE
CERTIFICATE OF CORRECTION

PATENT NO. : 7,405,227 B2  Page 1 of 1
APPLICATION NO. : 11/458379
DATED : July 29, 2008
INVENTOR(S) : Ernest Kun et al.

It is certified that error appears in the above-identified patent and that said Letters Patent is hereby corrected as shown below:

Title Page, in item (73) Assignee:
Change "BiPAr" to -- BiPar --

Column 37, line 49 "a ovarian cancer..." should be -- an ovarian cancer --

Signed and Sealed this

Thirtieth Day of September, 2008

JON W. DUDAS
*Director of the United States Patent and Trademark Office*

Disclaimer

7,405,227 B2 — Ernest Kun, Mill Valley, CA (US); Jerome Mendeleyev, San Francisco, CA (US); Carol Basbaum, San Francisco, CA (US); Hassan Lemjabbar-Alaoui, Foster City, CA (US); Valeria Ossovskaya, San Francisco, CA (US), TREATMENT OF CANCER. Patented date July 29, 2008. Disclaimer filed December 19, 2013 by the Assignee, BiPar Sciences, Inc.

Hereby enter this disclaimer to the entire term of said patent.

*(Official Gazette, April 1, 2014)*